United States Patent [19]

Fujino et al.

[11] Patent Number: 5,715,052
[45] Date of Patent: Feb. 3, 1998

[54] METHOD OF DETECTING THE POSITION AND THE CONTENT OF FINE FOREIGN MATTER ON SUBSTRATES AND ANALYZERS USED THEREFOR

[75] Inventors: Naohiko Fujino; Isamu Karino, both of Amagasaki, Japan

[73] Assignee: Mitsubishi Denki Kabushiki Kaisha, Tokyo, Japan

[21] Appl. No.: 867,387

[22] Filed: Jun. 2, 1997

Related U.S. Application Data

[63] Continuation of Ser. No. 451,659, May 30, 1995, abandoned.

[30] Foreign Application Priority Data

Jun. 2, 1994 [JP] Japan ............................ 6-121314

[51] Int. Cl.$^6$ ............................ G01N 21/00; G01B 11/14
[52] U.S. Cl. ................. 356/237; 356/375; 250/559.41; 250/559.45
[58] Field of Search ............................ 356/237, 239, 356/375; 250/559.41, 559.45, 559.46

[56] References Cited

U.S. PATENT DOCUMENTS

| | | | |
|---|---|---|---|
| 4,441,124 | 4/1984 | Heebner et al. | 356/237 |
| 4,595,289 | 6/1986 | Feldman et al. | 356/237 |
| 4,601,577 | 7/1986 | Gotou et al. | 356/237 |
| 4,764,969 | 8/1988 | Ohtombe et al. | |
| 4,766,324 | 8/1988 | Saadat et al. | 356/431 |
| 4,871,257 | 10/1989 | Suzuki et al. | 356/237 |
| 5,046,847 | 9/1991 | Nakata et al. | 356/237 |
| 5,117,110 | 5/1992 | Yasutake | 250/306 |
| 5,177,559 | 1/1993 | Batchelder et al. | 356/237 |
| 5,247,186 | 9/1993 | Toda | |
| 5,267,017 | 11/1993 | Uritsky et al. | 356/237 |
| 5,311,275 | 5/1994 | Taniguchi et al. | 356/237 |
| 5,321,495 | 6/1994 | Hgiwara et al. | 356/237 |
| 5,337,140 | 8/1994 | Hagiwara et al. | 356/237 |
| 5,379,347 | 1/1995 | Kato et al. | 356/237 |
| 5,422,724 | 6/1995 | Kinney et al. | 356/237 |

FOREIGN PATENT DOCUMENTS

| | | |
|---|---|---|
| 0 442 630 | 8/1991 | European Pat. Off. |
| 0 527 448 | 2/1993 | European Pat. Off. |
| 58-33154 | 2/1983 | Japan |
| WO85/03353 | 1/1985 | WIPO |

OTHER PUBLICATIONS

"Analysis and Evaluation Technology for High Performance Semiconductor Process", edited by Semiconductor Fundamental Technology Research Society, Published by Realize Ltd., pp. 111–129 in Japanese with brief English translation, May 29, 1992.

A. Abraitis et al., "Direct Readout Particle Detection System", *IBM Technical Disclosure Bulletin*, vol. 23, No. 11, Apr. 1981, pp. 4970–4971.

H. M. Marchman et al., "Optically Guided Large–Nanostructure Probe", *Review of Scientific Instruments*, vol. 64, No. 5, May 1993, New York, pp. 1248–1252.

"Analyzing and Estimating Technique for Processing High Performance Semiconductor", *Ultra Clean Tech.*, Series No. 13, Published by Realize Co., Ltd., 1992, pp. 110–129.

*Primary Examiner*—Frank G. Font
*Assistant Examiner*—Jason D. Vierra-Eisenberg
*Attorney, Agent, or Firm*—Burns, Doane, Swecker & Mathis, LLP

[57] ABSTRACT

Methods wherein a partial region of a fine foreign matter which is detected first in a particle counter is detected again, observed, analyzed and evaluated by irradiating a spot of beam light to the region, observing a scattered light from a dark field or a dark part in the spot from a blight field, a coordinate of the analyzer being linked with a coordinate of the partial counter and registered in the analyzer. Thereby semiconductor devices or liquid crystal display devices are inspected accurately and immediately.

59 Claims, 10 Drawing Sheets

METHOD OF DETECTING THE POSITION AND THE CONTENT OF FINE FOREIGN MATTER ON SUBSTRATES AND ANALYZERS USED THEREFOR

This application is a continuation of Application No. 08/451,659, filed May 30, 1995, now abandoned.

BACKGROUND OF THE INVENTION

The present invention relates to an analysis method of fine foreign matter existing on a flat sample surface such as silicon wafers or insulating transparent substrates, an analyzer and a method of manufacturing semiconductor devices or liquid crystal display devices by using a method and an analyzer.

More particularly, it relates to a method and analyzer for analyzing, inspecting and evaluating fine foreign matters specified by detecting and positioning by using a particle counter equipped with a defined coordinate system beforehand, by linking the specified position with a coordinate of the analyzer.

An analyzer in the specification means those devices in which particle beams with energy such as light, X-ray, electromagnetic wave, electron, neutral chemical species (atom, molecule), ion, phonon or the like are irradiated, afterwards secondary particle beams are detected which are emitted or absorbed after interaction with the sample surface, and then tone of color, steric image, elementary analysis, chemical structure or crystal structure are investigated or sample surfaces are processed.

Concrete examples are, for example, as follows: metallograph, laser microscope, Scanning Electron Microscope (SEM), Electron Probe Micro-Analyser (EPMA), X-ray Photoelecton Spectrometer (XPS), Ultraviolet Photoelectron Spectroscope (UPS), Secondary Ion Mass Spectroscope (SIMS), Time of Flight-SIMS (TOF-SIMS), Scanning Auger Electron Spectrometer (AES), Reflection High Energy Electron Diffraction (RHEED), Electron Energy-Loss Spectrometer (EELS), Focused Ion Beam instruments (FIB), Particle Induced X-ray Emission (PIXE), Microscope Fourier Transform Infrared Spectrometer ($\mu$ FTIR), Microscope Raman Spectrometer, Photoluminescence Spectrometer (PS), Infrared Spectrometer, Visible Spectrometer, Ultraviolet Spectrometer, Fluorescent Spectrometer.

The yield in manufacture of superhigh integration LSI represented by 4M, 16M bit-DRAM is said to depend mostly on defects due to foreign matters deposited on wafers.

This is because the foreign matters of micro size deposited on the wafer in the preceding manufacturing processes which did not matter hitherto, has come to be a contamination source as the pattern width becomes finer. The size of the fine foreign matter causing problems is generally said to be a factor of several times the minimum wiring width of the superhigh integration LSI to be manufactured, and hence in a 16M bit DRAM (minimum wiring width 0.5 $\mu$m), foreign matter of 0.1 $\mu$m in diameter is problematic. Such fine foreign matters become contaminants which cause breaking or shortcircuiting of the circuit pattern, leading to the onset of defects and lowering of quality and reliability. It is hence a key point in yield enhancement to measure and analyze the deposit state of fine foreign matters quantitatively and precisely, understand and control accordingly.

As the means thereof, conventionally, a particle counter capable of detecting the position of a fine foreign matter existing on the surface of flat sample such as a silicon wafer is used. Conventional particle counters include models IS-2000 and LS-6000 of Hitachi Electronic Engineering Co., model Surfscan 6200 of Tencor, and model WIS-9000 of Estek, both of the United States. The measuring principle of such particle counters and the construction of apparatus for realizing it are described for example, in "*Analysis and Evaluation Technology for High Performance Semiconductor Process,*" pages 111 to 129, edited by Semiconductor Fundamental Technology Research Society, published by Realize Ltd.

FIG. 9 shows the CRT display screen giving the result of measurement of fine foreign matters (0.1 $\mu$m or larger) existing on an actual 6-inch silicon wafer by using the particle counter LS-6000. The display screen shows only the approximate position of fine foreign matters, the quantity of each size, and distribution. The circle in FIG. 9 expresses the outer circumference of a 6-inch silicon wafer, and spots existing in the circle correspond to the existing positions of fine foreign matters. Particles and foreign matters mentioned herein denote bumps, recesses, deposited particles, and other defects on the wafer which differ from other parts, and portions causing light scattering.

However, as known from FIG. 9, as the information obtained from the conventional particle counter is only the size and position of the foreign matter, the content of the foreign matter is not identified.

For example, FIG. 10 is an explanatory diagram showing a fundamental structure of a conventional metallograph equipped with an actuator, as an example of metallograph equipped with positioning function used in conventional fine foreign matter detection, such as IC inspection microscopic system MODER IM-120 distributed by Nidec. In FIG. 10, a sample silicon wafer 2 is put on an x-y actuator 1 having coordinates roughly linked with coordinates of the particle counter. A foreign matter 7 detected by the particle counter is brought into the field of view of a metallograph 3 or its vicinity by the x-y actuator 1 on the basis of the positional information of the foreign matter obtained from the particle counter. Hereinafter, using the conventional metallograph equipped with an actuator, the inspection procedure and inspection result of the foreign matter 7 existing on a flat silicon wafer surface are explained.

First, a plurality of slightly stained mirror smooth polished silicon wafers 2 (Mitsubishi Material silicon made CZ (azimuth 100) 6-inch silicon wafers) are set in a particle counter (Surfscan 6200 of Tencor Untied States), and the size and rough positions of the foreign matter existing on the silicon wafer 2 are observed. On the silicon wafers 2, at random positions, there are about 800 foreign particles in the mean size of 0.1 to 0.2 $\mu$m level, abut 130 particles in the mean size of 0.2 to 0.3 $\mu$m level, about 30 particles in the mean size of 0.3 to 0.4 $\mu$m level, about 13 particles in the mean size of 0.4 to 0.5 $\mu$m and 15 particles in the larger size level. In the coordinates of Surfscan 6200, the direction adjoining the flat orientation of the wafer is the x-axis (or y-axis) direction, and the direction normal to the wafer surface is the y-axis (or x-axis) direction, and three or more points are measured on the outermost circumference of the wafer (avoiding the flat orientation portion), and by fitting the results to an equation of circle or ellipse, the system of coordinates is defined with the wafer center position as (0, 0).

Next, using a conventional metallograph equipped with an actuator, the direction adjoining the flat orientation of the wafer is defined to be the x-axis direction, and the direction normal to the wafer to be the y-axis (or x-axis) direction, and by measuring three point on the outermost circumference of the wafer (avoiding the flat orientation portion) and fitting the results to an equation of circle, a silicon wafer 2 is set on an x-y actuator 1 on the basis of the positional information of the foreign matter obtained from the particle counter, foreign particles of various sizes are observed by using a metallograph 3 (the magnification of the ocular lens is set at 20 times, and that of the objective lens is variable at 5,20 and 50 times to observe and evaluate).

As a result, using a 5 times magnification objective lens of metallograph, foreign matter of 0.4 to 0.5 μm level as a black spot can be barely observed, and smaller particles are hardly found. With a 50 times magnification objective lens, foreign matter of 0.2 to 0.3 μm level as a black spot can be barely found, and smaller particles are hardly noted.

Accordingly, concerning the individual fine foreign matters, by using a proper microscope or an analyzer, it is necessary to identify their nature by observing them directly or analyzing their composition. However, existing positions of individual foreign matters on the wafer obtained from the particle counter are defined by the coordinates of the particle counter, which may not always coincide with the coordinates of the analyzer which is not the particle counter. Moreover, the existing positions of individual fine foreign matters on the wafer are defined by the pixels (usually each region of 20 μm×200 μm) depending on the laser light focusing area on the wafers of the individual particle counters, and they involve, from the beginning, an error corresponding to the area of the pixels. When the samples such as wafers once inspected for foreign matter in the particle counter are set in a microscope or an analyzer other than the particle counter, an error is caused by deviation of the coordinates due to the new setting. It is hence necessary for identifying the nature of fine foreign matter to link, by some measure or other, the coordinates of the particle counter and the coordinates of the analyzer other than the particle counter such as a microscope, perfectly, so as to eliminate error depending on pixels, or to match the position of a fine foreign matter specified by the particle counter in the coordinates of analyzer other than a particle counter such as a microscope by newly recognizing them or another method so as to eliminate error. The laser light focusing area of the conventional particle counter is specifically described in "*Analysis and Evaluation Technology for High Performance Semiconductor Process,*" pages 111 to 129, edited by Semiconductor Fundamental Technology Research Society, published by Realize Ltd., and is about 20 μm×200 μm.

Investigations are then further made in the coordinates of the x-y stage of the particle counter, and the analyzer other than the particle counter such as a microscope. As a result, it is found that the coordinates of the x-y stages employed in almost all apparatuses are found to be the system of x-y coordinates. The method of determining the axes of coordinates and the origin of the apparatuses to the samples or wafers includes the following: (1) the direction adjoining the flat orientation of the wafer is the x-axis (or y-axis) direction, the direction normal to in the wafer surface is the y-axis (or x-axis) direction, the intersection of the outermost circumference of the wafer with the y-axis is (0, y), and the intersection with the x-axis is (x, 0), or (2) three or more points on the wafer outermost circumference are measured and fitted to an equation of circle or ellipse, and the wafer center position is defined as (0, 0).

In these methods, however, due to slight differences in surface precision or in size of the flat orientation of each wafer or outermost circumference each wafer, or deviation in setting the wafers on the sample table, or slight warp of wafer or the like, the axes of coordinates or the origin or central position may be deviated in every setting of each wafer, resulting in deviation in the axes of coordinates and origin to the individual wafers between the apparatuses (particle counter and analyzer) employing this method. The extent of deviation caused by the abovementioned reasons is investigated in various apparatuses by using a plurality of wafers having lattice patterns, it is found that there is a deviation of about (±100 μm, ±100 μm) to the origin, central position or an arbitrary point defined therein, in the expression of x-y coordinates even between apparatuses of high precision (particle counter model IS-2000 of Hitachi Electronic Engineering, and length measuring SEM model S-7000 of Hitachi, Ltd.). Accordingly, relating to a fine foreign matter on an arbitrary position on the wafer detected by the particle counter, when it is desired to evaluate by observing or analyzing by means of an analyzer, it is necessary to observe at least in a range (200 μm×200 μm=40,000 μm$^2$) (field of view of SEM in magnification× 500 of SEM) over (±100 μm, ±100 μm), centered on the estimated existing position of the fine foreign matter detected by the particle counter, to confirm the position of the fine foreign matter, by means of an analyzer, and to observe or analyze the fine foreign matter or the like, which is the initial purpose, by magnifying the area or the like, and thereby evaluating. It must take a considerable long detection time.

To directly observe the size of this region as compared with the fine foreign matter, in this range of 40,000 μm$^2$ (200 μm×200 μm), assuming the observation is by use of a CCD camera of 1,000,000 pixels which is regarded to be a CCD camera of a relatively high resolution at the present, the size of the smallest fine foreign matter which can be detected is considered by calculating the detection region (area) occupied by the pixels of the CCD camera.

The calculation result is that the area of the detection region is 0.04 μm$^2$ (40,000 μm$^2$÷1,000,000=0.2 μm×0.2 μm). On the other hand, a particle smaller than one pixel is hard to be distinguished, and hence the detection limit of the fine foreign matter is 0.04 μm$^2$ (0.2 μm×0.2 μm). That is, it is difficult to detect a fine foreign matter of which the projection area is less than 0.04 μm$^2$ (diameter about 0.2 μm) directly by using a CCD camera with 1,000,000 pixels, and it is also known hard to specify the position of such fine foreign matter. Hence, it is almost impossible to identify the position of a fine foreign matter of 0.2 μm or less.

Accordingly, concerning a fine foreign matter of about 0.2 μm or less in diameter detected in a conventional particle counter, by linking with the coordinates of the analyzer on the basis of the coordinates of the particle counter, it may be understood that it is generally difficult to observe or evaluate the fine foreign matter directly by specifying the position of the fine foreign matter.

The invention is intended to solve the abovementioned problems, and it is hence a primary object to present a method for positioning fine foreign matters and analyzer for observation, analysis and evaluation of the fine foreign matters by detecting again the fine foreign matter on the coordinates of the analyzer, relating the fine foreign matter of which the position is determined to the coordinates of the particle counter, and registering the position of the fine foreign matter precisely in the coordinates of an analyzer.

It is the second object of the invention to present an analysis method of a fine foreign matter and an analyzer used therefor so as to observe, analyze, and evaluate the fine foreign matter, by newly discovering the fine foreign matter in the coordinates of the analyzer, and registering the position of fine foreign matter precisely in the coordinates of an analyzer.

It is the other object of the invention to present a manufacturing method of semiconductor devices and liquid crystal display devices. The method enhances the yield and the reliability of semiconductor devices or liquid crystal display devices, by analyzing the foreign matter by the analyzer, in a process of manufacturing semiconductor devices or liquid crystal display devices.

SUMMARY OF THE INVENTION

The positioning method of a fine foreign matter according to the present invention is a method comprising:
(a) determining a position of the fine foreign matter on a sample surface in a particle counter,
(b) transferring the sample onto a coordinate stage of an analyzer,
(c) linking the position determined by the particle counter with a coordinate of a coordinate system on the coordinate stage of the analyzer roughly,
(d) irradiating a spot of beam light to a partial region on the sample surface including the coordinate relating to the position of the fine foreign matter determined by the particle counter,
(e) detecting again the position of the fine foreign matter by observing a change in the beam light caused by the fine foreign matter, that is, by observing an irregular reflection light by the fine foreign matter or a dark area in a spot region irradiated by the beam light, and
(f) registering the position of the fine foreign matter detected again in the coordinate of the analyzer.

The analysis method of a fine foreign matter according to the present invention is a method comprising:
(a) determining a position of the fine foreign matter on a sample surface in a particle counter,
(b) transferring the sample onto a coordinate stage of an analyzer,
(c) linking the position determined by the particle counter with a coordinate of a coordinate system on the coordinate stage of the analyzer roughly,
(d) irradiating a spot of beam light to a partial region on the sample surface including the coordinate relating to the position of the fine foreign matter determined by the particle counter,
(e) detecting again the position of the fine foreign matter by observing a change in the beam light caused by the fine foreign matter,
(f) registering the position of the fine foreign matter detected again in the coordinates of the analyzer
(g) irradiating a portion of the surface of the sample which includes the position of the fine foreign matter detected again with the beam light and
(h) analyzing the content of the fine foreign matter.

The analyzer according to the present invention is an analyzer for analysis of surface condition of the sample by irradiating a particle beam to both an x-y stage which can be moved at least longitudinally and laterally and a sample located on the x-y stage and observing the secondary particle beam emitted from the sample further comprising:
(a) a beam light source for foreign matter detection for detecting foreign matter on the sample surface, and
(b) a detector of the beam light for detecting a change in the beam light from the source of beam light caused by the foreign matter on the sample surface.

The manufacturing method of semiconductor devices according to the present invention is a method comprising the steps of at least a cleaning step, a film forming step, an exposure step, a etching step, an ion implantation step, a diffusion step, and a heat treatment step wherein at least one of the steps is accompanied by inspection substeps, at least one of the substeps being an analysis substep wherein an analysis for analyzing a foreign matter is carried out by means of a method comprising:
(a) determining a position of the fine foreign matter on a sample surface in a particle counter,
(b) transferring the sample onto a coordinate stage of an analyzer,
(c) linking the position determined by the particle counter with a coordinate of a coordinate system on the coordinate stage of an analyzer roughly,
(d) irradiating a spot of beam light to a partial region on the sample surface including the coordinate relating to the position of the fine foreign matter determined by the particle counter,
(e) detecting again the position of the fine foreign matter by observing a change in the beam light caused by the fine foreign matter,
(f) registering the position of the fine foreign matter detected again in the coordinates of the analyzer,
(g) irradiating a portion of the surface of the sample which includes the position of the fine foreign matter detected again with the beam light and
(h) analyzing the content of the fine foreign matter.

The manufacturing method of liquid crystal display devices according to the present invention is a method for manufacturing liquid crystal display devices comprising:
(a) adhering TFT substrate of a first insulating transparent substrate on which at least thin film transistors and pixel electrodes are provided, and a counter substrate of a second insulating transparent substrate on which counter electrodes are provided on their circumference while keeping a specific clearance between the two substrates, and
(b) injecting liquid crystal material in the clearance, the method further includes a cleaning step, a film forming step, an exposure step, an etching step, an ion implantation step, and a heat treatment step for manufacturing the TFT substrate and the counter substrate, at least one of the steps is accompanied by inspection substeps, and at least one of the substeps is an analysis substep wherein an analysis for analyzing the foreign matter is carried out by means of method comprising:
(1) determining a position of a fine foreign matter on a sample surface in a particle counter,
(2) transferring the sample onto a coordinate stage of an analyzer,
(3) linking the position determined by the particle counter equipped with a coordinate of a coordinate system on the coordinate stage of an analyzer roughly,
(4) irradiating a spot of beam light to a partial region on the sample surface including the coordinate relating to the position of the fine foreign matter determined by the particle counter,
(5) detecting again the position of the fine foreign matter by observing a change in the beam light caused by the fine foreign matter
(6) registering the position of the fine foreign matter detected again in the coordinates of the analyzer,
(7) irradiating a portion of the surface of the sample which includes the position of the fine foreign matter detected again with the beam light and
(8) analyzing the content of the fine foreign matter.

To analyze the fine foreign matter in the manufacturing method of the semiconductor devices and in the manufacturing method of liquid crystal display devices, by using the abovementioned analyzer, and more specifically by using a proper one of the analyzers, the surface shape of the fine foreign matter, elementary analysis, chemical composition, and crystal structure can be analyzed, while surface processing can be done.

For the fine foreign matter located on the coordinates of the particle counter of the invention, according to the positioning method of the fine foreign matter for determining the position of the fine foreign matter precisely on the coordinates of the analyzer, in a range on the sample surface covering the deviation caused by roughly linking the coordinates of the conventional particle counter with the coordinates of the analyzer, by spot irradiation of beam light for detecting the fine foreign matter and detecting of the beam light reflected by the fine foreign matter from the dark field or bright field, the existing position of the fine foreign matter is detected, and hence the existing position of the fine foreign matter can be registered precisely in the coordinates of the analyzer. In the observation of irregular reflection light from the dark field, a higher contrast ratio is easily obtained by the observation of dark area by bright field.

According to the analysis method of the fine foreign matter of the invention, since the position of the fine foreign matter is easily specified in the coordinates of the analyzer by the positioning method of the fine foreign matter mentioned above, the particle beam of the analyzer can be accurately irradiated toward the fine foreign matter, so that the state of the fine foreign matter can be easily analyzed.

In the analyzer of the invention, which comprises a beam light source for foreign matter detection and a detector of the beam light for detecting from the source of the beam light due to the foreign matter in addition to the conventional analyzer, an approximate position of the fine foreign matter detected by the particle counter, and positional deviation when moved to the analyzer are immediately corrected, and the position of the fine foreign matter is determined (registered again) in the correct coordinates of the analyzer, and the particle beam for analysis can be irradiated accurately toward the fine foreign matter. As a result, the state of the fine foreign matter can be investigated easily and accurately.

According to the method of manufacturing semiconductor devices of the invention, since the state of the fine foreign matter on the wafer surface can be inspected in the midst of the manufacturing process either by sampling or by 100% situation, the occurrence and the cause of the occurrence of the fine foreign matter in the manufacturing process can be known, so that the data can be immediately fed back to the manufacturing process. As a result, in the super LSI in the sub-micron order wiring, defects due to the fine foreign matter may be kept to a minimum limit, and the yield can be enhanced while the reliability is enhanced.

Further according to the method of manufacturing liquid crystal display devices of the invention, the existence of the fine foreign matter can be known in the midst of the forming process of thin film transistors or signal wiring, and wire breakage and other accidents can be prevented in the liquid crystal display devices of fine wiring in the high definition tendency, and the yield and reliability of the liquid crystal display devices are improved.

DETAILED DESCRIPTION

Figure 1:
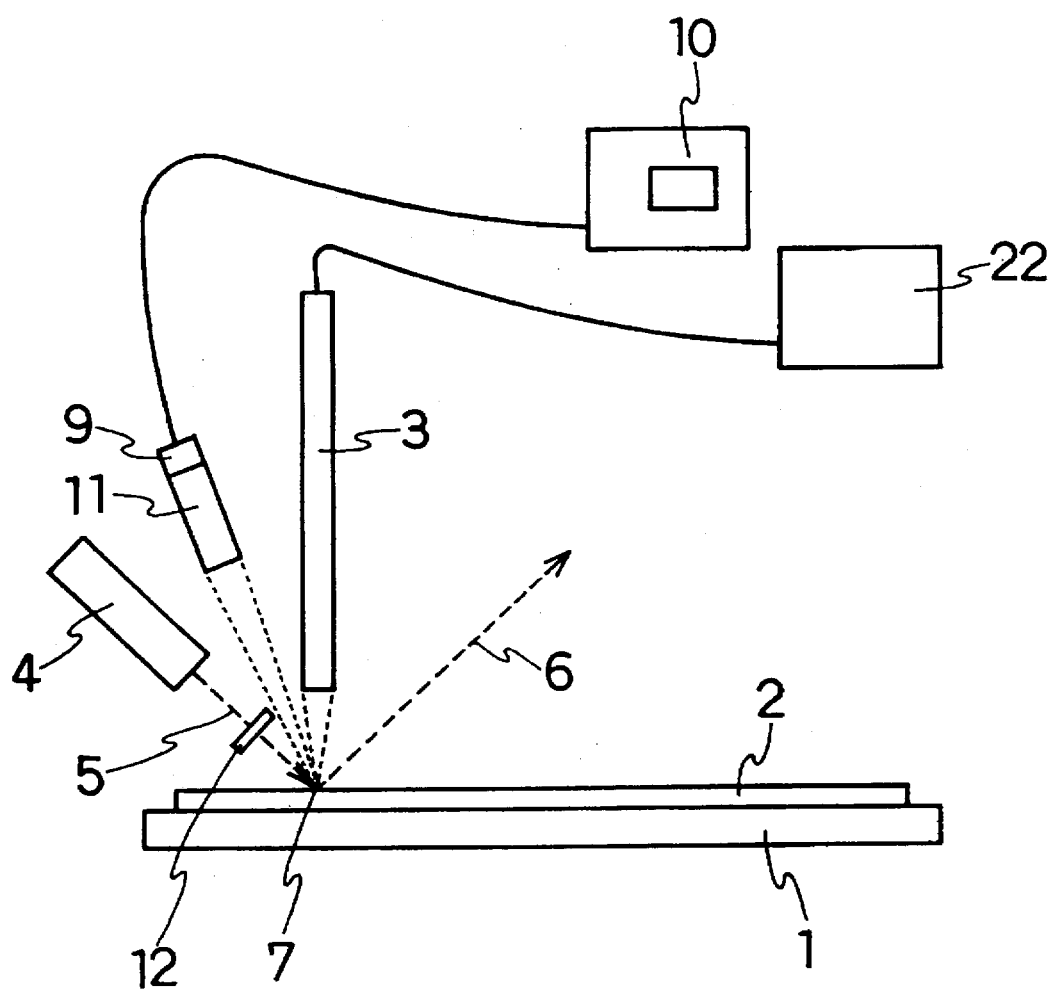
FIG. 1 is an explanatory diagram showing an example of observation method of fine foreign matter from dark field.

Described below are the positioning method and analysis method of the fine foreign matter of the invention and analyzer therefor, and a method of manufacturing semiconductor devices and liquid crystal display devices employing the same.

The method of determining the fine foreign matter of the invention is to determine the position of the fine foreign matter on a sample surface in a particle counter, transfer the sample onto a coordinate stage of an analyzer, irradiate a spot of beam light to a partial region on the sample surface including the position of the fine foreign matter which is determined in the particle counter, detect the fine foreign matter again, and determine (register again) the position of the fine foreign matter in the coordinates of the analyzer.

According to the analysis method of the fine foreign matter of the sample, the position of the fine foreign matter is positioned with the irradiation area of the particle beam of the analyzer after the abovementioned positioning, and the content of the fine foreign matter is analyzed.

If the deviation caused when the coordinates of the conventional particle counter are linked with the coordinates of the analyzer is, for example, thousands of microns, in the range on the sample surface covering it, by spot irradiation of the beam light for detecting the fine foreign matter (for example, a field of view of thousands of microns can be covered by using an objective lens of about 5 times magnification), the presence of the fine foreign matter on the coordinates of the analyzer can be detected, and hence the position of the fine foreign matter can be accurately determined and registered on the x-y coordinates of the analyzer.

By irradiating the beam light for detecting the foreign matters and detecting the beam light reflected from the sample surface from the bright field, for example, if there is a foreign matter somewhere on the irradiated position, the beam light is scattered in that position in a form depending on the surface shape of the fine foreign matter or the like, and hence the optical axis of the light irradiated on the fine foreign matter is distorted, and it is largely offset from the sample surface other than the fine foreign matter. Hence, inside the spot observed from the bright field, an isolated portion of normal reflection by the fine foreign matter appears, and this portion becomes dark, thus suggesting the existing position of the fine foreign matter or the like. Accordingly, from the bright field, a dark part is observed in the spot (incidentally, the position of dark part in the spot observed from the bright field coincides with the existing position of the fine foreign matter or the like). As a result, by detecting the beam light reflected from the sample surface from the bright field, the existing position of the fine foreign matter can be registered in the coordinates of the analyzer easily and precisely as (x, y). If, accordingly, the deviation caused by linking the coordinates of the conventional particle counter with the coordinates of the analyzer is large, by observing the dark part inside the spot easily from the bright field, concerning the fine foreign matter the position of which is determined on the coordinates of the particle counter, the fine foreign matter detected by the particle counter can be registered precisely in the coordinates of the analyzer.

As the method of detecting the dark part in the spot due to the fine foreign matter by the beam light for detecting the fine foreign matter, the beam light is passed through a polarizing plate, and the beam light of S-polarized light is used on the sample surface such as wafers, and hence the directivity of the irregular reflection light is enhanced, and the contrast ratio of the dark part in the spot to the other area is emphasized, so that the fine foreign matter may be detected more easily.

Also as the method of detecting the dark part in the spot due to the fine foreign matter by the beam light for detecting the fine foreign matter, the beam light is used as the laser light, and hence the directivity of the light is further enhanced, and thereby the contrast ratio of the dark part in the spot to the other area is emphasized, so that the fine foreign matter may be detected more easily.

Moreover, as the method of detecting the dark part in the spot due to the fine foreign matter by the beam light for detecting the fine foreign matter, the laser light is passed through a polarizing plate, and the laser light of S-polarized light is used on the sample surfaces such as wafers, and hence the directivity of the irregular reflection light is enhanced, and the contrast ratio of the dark part in the spot to the other area is emphasized, so that the fine foreign matter may be detected more easily.

The dark part in the spot from the bright field can be detected easily and securely, by disposing the microscope in the bright field, matching the focus of the microscope with the reflecting position of the beam light on the sample surface, and disposing the light detecting elements such as photodiodes and phototransistors opposite to the position reflected on the sample surface.

For easier observation by the microscope, or for the sake of keeping the observer safe from the beam light, a CCD camera can be attached on the CRT.

As the CCD camera, in order to detect a feeble irregular reflection light, it is preferred to use a CCD camera on which an image intensifier is mounted.

To detect the fine foreign matter in the method of the invention, in the range on the sample surface covering the deviation caused by linking roughly the coordinates of the conventional particle counter and the coordinates of the analyzer, by irradiating beam light for detecting foreign matters so as to detect the beam light reflected from the sample surface from the dark field, the existing position of the fine foreign matters can be detected. For example, if there is a foreign matter somewhere on the irradiated position, the beam light is irregularly reflected in that area, and the irregular reflection light from the dark field is observed in a form depending on the surface shape of the fine foreign matter. Accordingly, by detecting the beam light reflected from the sample surface from the dark field, the existing position of the fine foreign matter can be registered in the coordinates of the analyzer such as a microscope, other than the particle counter, easily and precisely as ($x_1$, $y_1$). Hence, if the deviation is large when linking the coordinates of the conventional particle counter and the coordinates of the analyzer, by observing the irregular reflection light easily from the dark field, the fine foreign matter positioned on the coordinates of the particle counter can be precisely registered as the position of the foreign matter detected by the particle counter in the coordinates of the analyzer.

As the method for detecting the irregular reflection light from the dark field due to the fine foreign matter by the beam light for detecting the fine foreign matter, the beam light is passed through a polarizing plate, and the beam light of S-polarized light to the sample surface such as wafers are used, and hence the directivity of the irregular reflection light (scatter of light) is enhanced, and the stray light to the irregular reflection light can be decreased. As a result, the fine foreign matter can be detected more easily.

As the method of detecting the irregular reflection light from the dark field due to the fine foreign matter by the beam light for detecting the fine foreign matter, the beam light is replaced by a laser light, and the light directivity is enhanced, so that the fine foreign matter can be detected more easily.

As the method for detecting the irregular reflection light from the dark field due to the fine foreign matter by the beam light for detecting the fine foreign matter, the laser light is passed through a polarizing plate, and the beam light of S-polarized light to the sample surfaces such as wafers are used, and hence the directivity of the irregular reflection light (scatter of light) is enhanced, and the stray light to the irregular reflection light can be decreased, and therefore the fine foreign matter can be detected more easily.

To detect the irregular reflection light from the dark field, the photodetectors such as microscopes, photodiodes, and phototransistors are disposed in the dark field, and the focus of the microscope is adjusted to the reflecting position of the beam on the sample surface, or the photodetectors such as photodiodes are set opposite to the reflecting position on the sample surface, so that it can be detected easily and securely.

For easier observation by the microscope, or for the sake of keeping the observer safe from the beam light, a CCD camera can be attached to the ocular (or eyepiece) of the microscope, and this image information is displayed on the CRT to secure safety.

As the CCD camera, in order to detect a feeble irregular reflection light, it is preferred to use a CCD camera on which an image intensifier is mounted.

In the means for positioning fine foreign matter of the invention, by spot irradiation of beam light for detection of fine foreign matter and observation of change in beam light due to the fine foreign matter, after detecting the fine foreign matter, the position of the foreign matter is determined, and therefore if the intended fine foreign matter cannot be detected by the particle counter, the presence can be detected on the coordinates of the analyzer, so that the position of the fine foreign matter can be newly determined on the basis of this information.

Referring now to the drawings, the positioning method and analysis method of a fine foreign matter are more specifically described below by using a practical analyzing apparatus.

Example 1

FIG. 1 is an explanatory diagram showing a fundamental constitution of an analysis method of the fine foreign matter of the invention. In FIG. 1, reference numeral 4 is an Ar laser (with an output of 15 mW) provided for irradiating inspection beam light 5 for inspecting a foreign matter 7 existing on the surface of a flat silicon wafer. The inspection beam light 5 can be polarized by a polarizing plate 12. Reference numeral 11 is a microscope provided for observing a surface position (spot 13) of the sample 2 made of, for example, a silicon wafer, illuminated with the Ar laser 4 from a dark field. Both centers of fields of view of the microscope 11 and analyzer 3 are arranged to coincide nearly with each other. A CCD camera 9 on which an image intensifier is mounted is attached to the microscope 11, and an image of the observed position is displayed on an CRT 10. Reference numeral 1 is an x-y actuator on which the silicon wafer 2 is placed. Reference numeral 22 is a display unit of output data of an analysis unit 3. Using the analyzer of the inventions, hereinafter, the inspection procedure and inspection result of inspecting the foreign matter 7 existing on the surface of the sample 2 which is a flat silicon wafer are described below.

In the first place, the sample (hereinafter called silicon wafer) 2 is set on the x-y actuator 1 of the analyzer of the invention according to the conventional setting procedure.

By driving the x-y actuator 1, the surface position of the silicon wafer 2 which is considered to comprise the foreign matter 7, the coordinates of which are roughly observed preliminarily by a particle counter is moved to the irradiated position (spot 13) of the foreign matter detection beam light 5.

Figure 2:
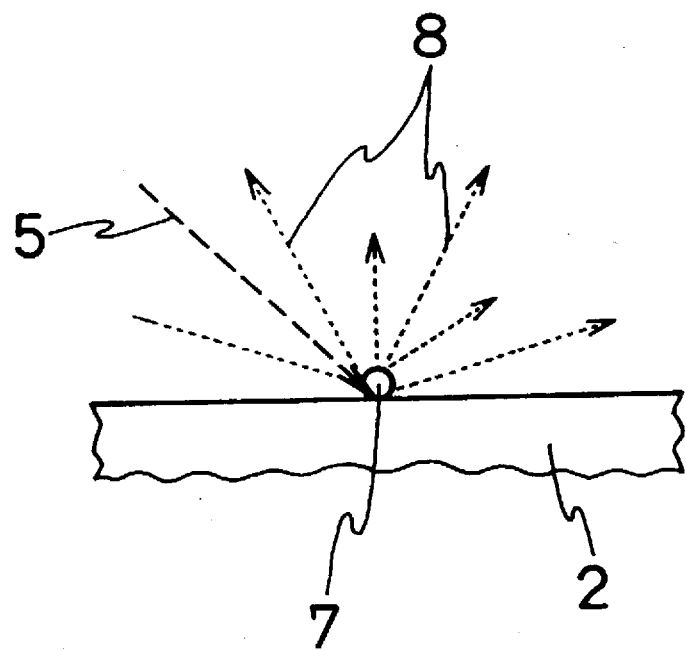
FIG. 2 is a schematic diagram showing an example of observation of the irregular reflection light from a side view.
Figure 3:
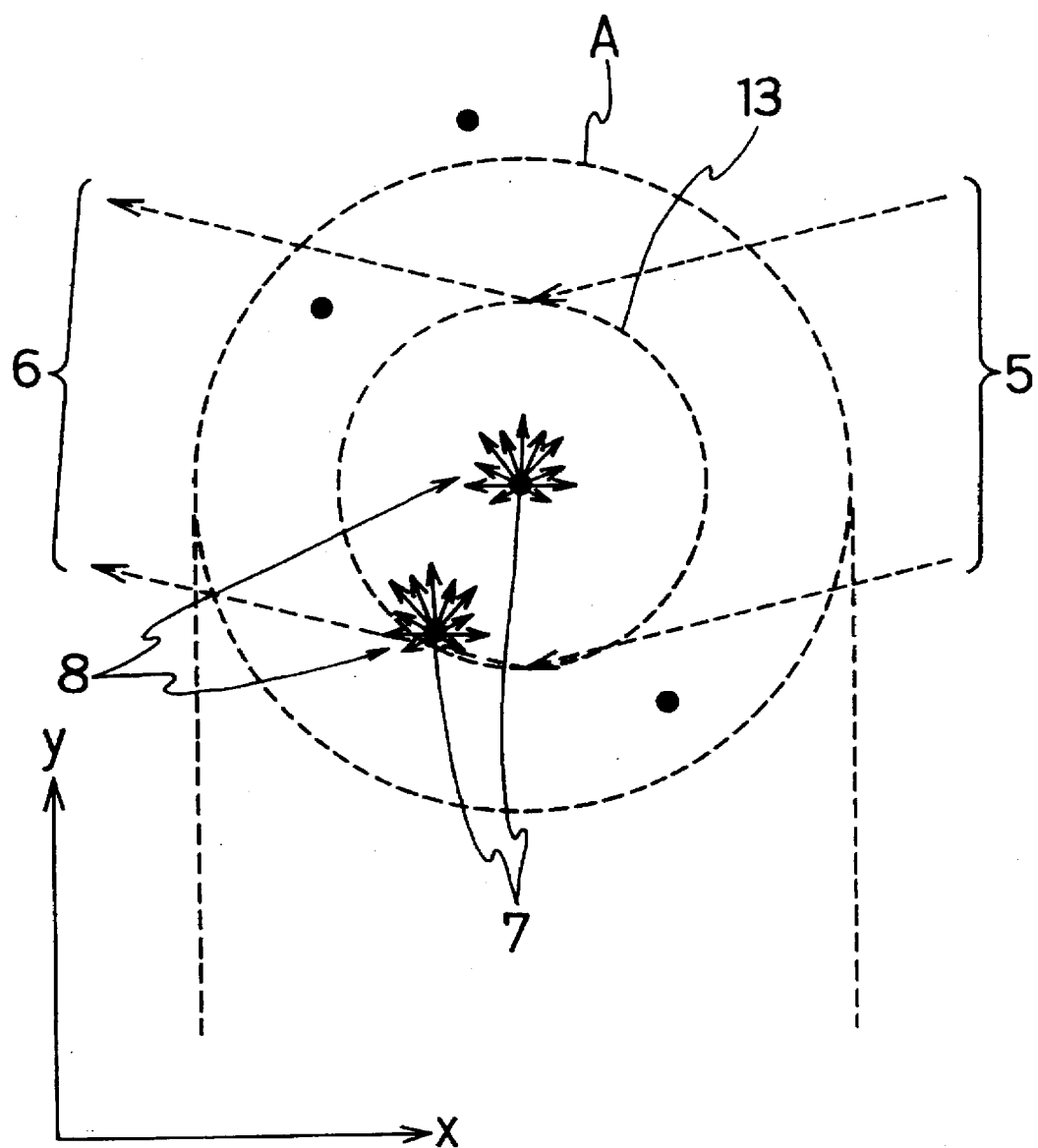
FIG. 3 is a schematic diagram showing an example of observation of the irregular reflection light from a dark field.

Next, while manipulating the x-y actuator 1 in the x-y direction, the surface of the silicon wafer 2 is observed from the dark field. If the foreign matter 7 is present on the optical path, the irregularly reflected light 8 is observed on the coordinates $(x_1, y_1)$ of the x-y actuator 1 (see FIG. 2). At this time, if the foreign matter 7 does not exist on the optical path, the foreign matter detection beam light 5 is reflected normally on the surface of the silicon wafer 2, therefore the reflected beam light 6 cannot be observed from the dark field. This relation is further described below. FIG. 3 is a schematic diagram of observing from the dark field the beam light irradiation position the surface of the silicon wafer 2 being irradiated by the detection beam light 5, and the irregularly reflected light 8 showing the foreign matter existing there by the microscope 11. In the observation system in FIG. 3, the observation field range A of the microscope 11 installed in the dark field is shown to cover the spot diameter 13 on the silicon wafer 2 on which the detection beam light 5 is irradiated. As known from FIG. 3, the existing position of the foreign matter 7 inside the spot diameter 13 can be identified by observing irregularly reflected light 8 by the microscope 11 because of the generation of the irregularly reflected light 8 in the silicon wafer 2. Within the same spot diameter 13, on the other hand, in the portion free from foreign matter 7, the beam of the detection beam light 5 is completely reflected normally, and nothing is observed by means of the microscope 11 installed in the dark field. Hence, using the detection beam light 5 of far larger spot diameter 13 than the foreign matter, the irregularly reflected light 8 by the foreign matter 7 can be observed by means of the microscope 11 installed in the dark field, and the position in the spot diameter 13 can be easily identified with great precision.

In the silicon wafer 2 evaluated herein, meanwhile, at an estimated position of the foreign matter 7 on the surface of the silicon wafer 2 after roughly observing the coordinates preliminarily by the particle counter, the irregularly reflection light is confirmed securely at one position or more in the field of view in a range of about 2 mm in diameter being covered by the microscope 11 (observed with the ocular lens magnified 5 times magnification and objective lens fixed at 20 times magnification). The intensity of the observed irregularly reflected light 8 is increased, and the output of the Ar laser 4 is intensified, and is stronger if the foreign matter is of the 0.2 to 0.3 μm level than if the foreign matter is of the 0.1 to 0.2 μm level. The intensity of the irregularly reflected light 8 displayed from the CRT 10 is stronger as the detection sensitivity of the CCD camera 9 on which an image intensifier is mounted is enhanced, and it is the strongest when the foreign matter detection beam light 5 has been polarized as S-polarized light on the surface of the silicon wafer 2 by the polarizing plate 12, and the S/N ratio is also high. Assuming the position nm where the irregularly reflected light 8 is observed to be the existing position of the foreign matter n, and bringing it onto the center of the field of the microscope 11, it is registered as the existing position of the foreign matter n in the coordinates $(x_n, y_m)$ of the x-y actuator 1. On the basis of the coordinates $(x_n, y_m)$ of the x-y actuator, each foreign matter is analyzed by means of the analyzing unit 3.

In this example, the fine foreign matter is analyzed by means of a metallograph as the analyzing unit 3. In this case, by using a conventional objective lens of 5 times magnification, the surface of the foreign matter 7 of 0.5 μm or larger particle size can be observed. Also, the surface of the foreign matter 7 of smaller than 0.5 μm can be absorbed as a black spot. However, since the location of the foreign matter 7 is known according to the constitution of the invention, and the objective lens of higher magnification can be used, determination of presence or absence of fine foreign matters which are hard to identify by means of the conventional apparatus can be performed.

Instead of observing the irregularly reflected light 8 by the foreign matter 7 by means of the microscope 11 herein, it can be observed directly by means of the metal microscope as the analyzing unit 3.

By means of the metallograph, interference fringe can be also observed, and it is effective for analysis of thickness in the heightwise direction of the foreign matter. Particularly it is effective when it is used in analysis of the foreign matter after film forming process in foreign matter analysis of semiconductor wafers or insulating transparent substrates.

Example 2

Figure 4:
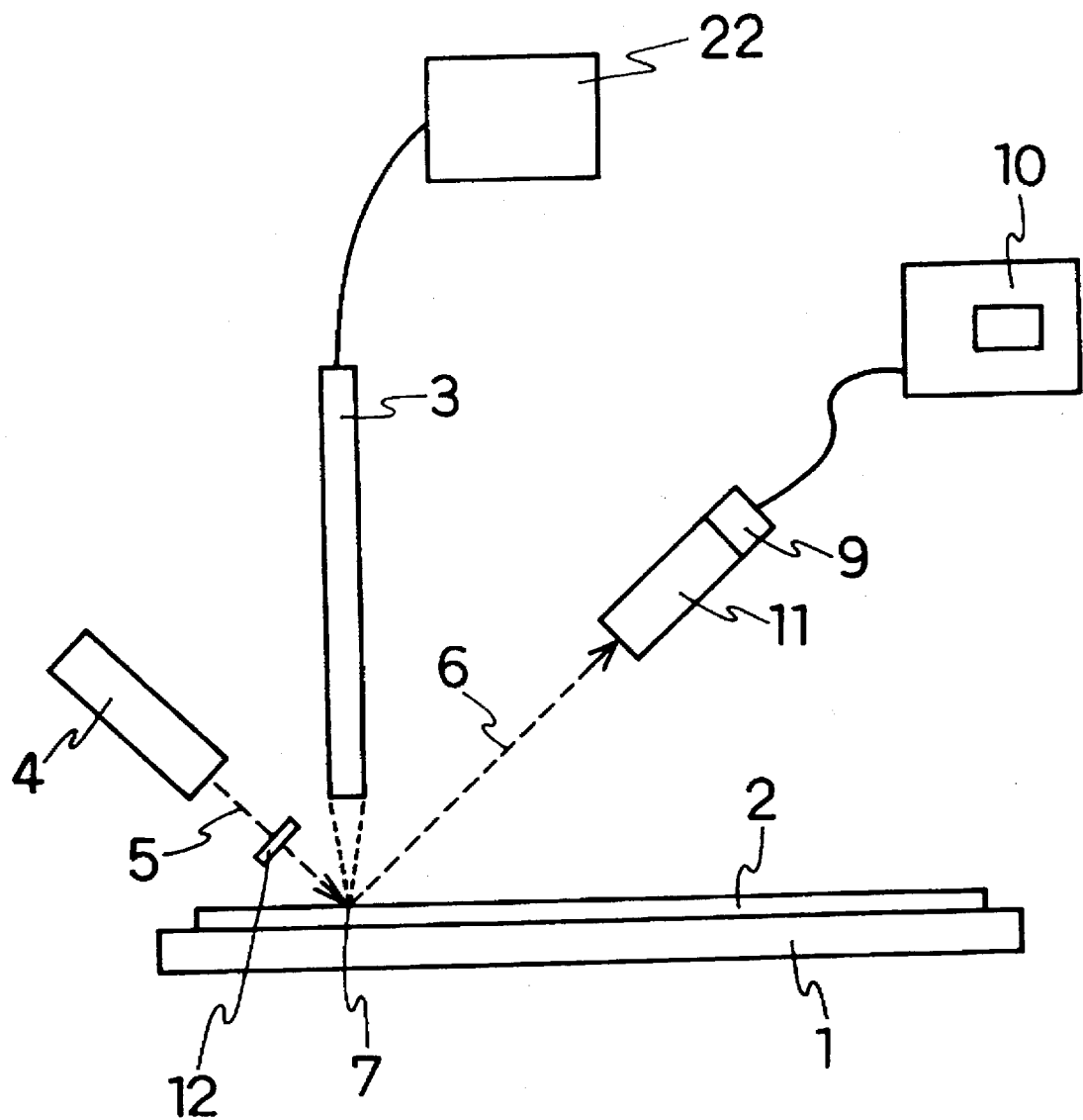
FIG. 4 is an explanatory diagram showing an example of an observation method of fine foreign matter from a bright field.
Figure 5:
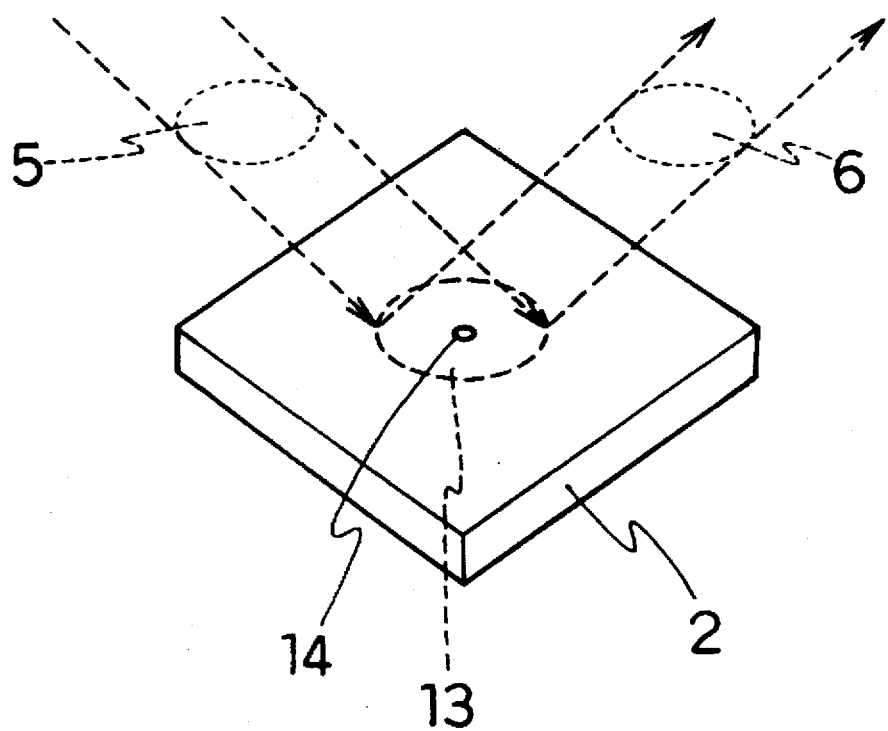
FIG. 5 is a schematic diagram of an example of observation of a dark area from a bright field.

FIG. 4 is an explanatory diagram showing another fundamental constitution of a method of analysis of fine foreign matters of the invention. The difference between this example 2 and the constitution of example 1 is that the microscope 11 installed in the dark field in example 1 is moved and installed in the bright field in which the microscope is capable of receiving the reflected beam light 6 in example 2. Hence, the constitution of the apparatus is the same except for the location of the microscope 11 (difference of dark field and bright field). When the reflected beam 6 is observed by microscope 11 from the bright field, a dark area 14 is observed. In the portion of the foreign matter 7 (see FIG. 5). Thus, the coordinates $(x_1, Y_1)$ of the position of observing the dark area 14 can be known. At this time, if there is no foreign matter 7 on the spot diameter 13, detection beam light 5 is normally reflected on the surface of the wafer 2, and hence dark area 14 cannot be observed from the bright field. Therefore, if the detection beam light 5 of spot diameter much larger than the foreign matter is used, the dark area 14 due to the foreign matter 7 can be observed by means of the microscope 11 installed in the bright field, so that the position in the spot diameter 13 can be identified easily with great precision. The other positioning procedure is the same as in example 1.

In the silicon wafer 2 evaluated herein, meanwhile, at an estimated position of foreign matter 7 on the surface of the silicon wafer 2 after roughly observing the coordinates preliminarily determined by the particle counter, the dark area 14 is confirmed securely at one position or more in the field of view in a range of about 0.2 mm in diameter being covered by the microscope 11 (observed with the ocular lens magnified 50 times and objective lens fixed at 20 times). The contrast of the observed dark area 14 is higher for foreign matters of the 0.2 to 0.3 µm level than for the foreign matter of the 0.1 to 0.2 µm level. When the foreign matter detection beam light is polarized as S-polarized light on the surface of the silicon wafer by the polarizing plate 12, it is the strongest, and the S/N ratio is also high. Assuming the position nm where the dark area 14 is observed to be the existing position of foreign matter n, and bringing it onto the center of the field of the microscope 11, it is registered as the existing position of the foreign matter n in the coordinates $(x_n, y_m)$ of the x-y actuator 1. On the basis of the coordinates $(x_n, y_m)$ of the x-y actuator 1, each foreign matter is analyzed by means of the analyzing unit 3.

In the example, by means of a metallograph as the analyzing unit 3, together with a conventional objective lens of 5 times magnification, the surface of the foreign matter 7 of 0.5 µm or larger particle size can be observed. Also presence or absence of the foreign matter of smaller than 0.5 µm is also recognized, and the same result as in example 1 is obtained.

Example 3

In this example, instead of the metallograph in example 1, a Scanning Laser Microscope is used, and the other constitution is the same as in FIG. 1, and the positioning operation method is also the same as in example 1.

As the Scanning Laser Microscope for example, model RCM 8000 of Nikon may be used. When it is combined with, for example, an Ar laser 4 for a beam light source for foreign matter detection and microscope 11 as a detector of the beam light which is the same as in the foregoing examples, the Scanning Laser Microscope apparatus of the invention is constituted.

Using UV light in measurement, as a result of observation of each foreign matter 7, the surface of the foreign matter of 0.2 µm level or more can be observed, and the dark spot in the region of the particle size can be also found in the foreign matter of less than 0.2 µm.

It is a feature of the example that the surface can be observed nondestructively and in the atmosphere, and when it is used in the process for manufacturing of semiconductor devices or liquid crystal display devices, it is particularly effective in analysis of the foreign matters in the steps after film forming step.

In this example, the position of the foreign matter is identified by observing the irregular reflection light by the foreign matter in the dark field by the microscope 11, but the same effect is obtained by detecting dark area of the reflected light by means of the microscope 11 installed in the bright field which is the same as in example 2.

Example 4

In the example, as the analyzing unit 3, instead of the metallograph in example 1, a Microscope FTIR is used, and the other constitution is the same as in FIG. 1, and the positioning operation method is also the same as in example 1.

As the Microscope FTIR model JIR-5500 on which microscopic infrared unit IR-MAU110 of Nippon Denshi is mounted may be used. When it is combined with, for example, an Ar laser 4 for a beam light source for foreign matter detection and microscope 11 as a detector of the beam light which is the same as in the foregoing examples, the Microscope FTIR apparatus equipped with positioning function of the invention is constituted.

According to the example, the IR spectrum characteristic of organic matter is obtained from several foreign matters 7 in 3 µm level, and the cause of occurrence of foreign matter is found to depend on the defect in the resist removal step. This analysis is effective in the process for manufacturing semiconductor devices or liquid crystal display devices, and in particular in the step after the resist coating step.

In this example, the irregular reflection light from the position of the foreign matter is identified by observing the reflected light by the foreign matter in the dark field by means of the microscope 11, but the same effect is obtained by detecting dark area of the reflected light by the microscope 11 installed in the bright field which is the same as in example 2.

Example 5

In the example, as the analyzing unit 3, instead of the metallograph in example 1, a Microscope Raman Spectrometer is used, and the other constitution is the same as in FIG. 1, and the positioning operation method is also the same as in example 1.

As the Microscope Raman Spectrometer for example, model NR-1800 of Nippon Bunko may be used. When it is combined with, for example, an Ar laser 4 for a beam light source for foreign matter detection and microscope 11 as a detector of the beam light which is the same as in the foregoing examples, the Microscope Raman Spectrometer equipped with positioning function of the invention is constituted.

According to the example, the Raman spectrum characteristic of inorganic matter is obtained among several foreign matters 7 in the 1 µm level, and the foreign matter is found to be an inorganic matter and the cause of the occurrence of which is related with dust in film formation step. This analysis is effective in the process for manufacturing semiconductor devices or liquid crystal display devices, in particular in the steps relating to film forming, etching, and heat treatment.

In this example, the position of the foreign matter is identified by observing the irregular reflection light by the foreign matter in the dark field by means of the microscope 11, but the same effect is obtained by detecting dark area of the reflected light by means of the microscope 11 installed in the bright field which is the same as in example 2.

Example 6

In the example, as the analyzing unit 3, instead of the metallograph in example 1, a PL measuring instrument is used, and the other constitution is the same as in FIG. 1, and the positioning operation method is also the same as in example 1.

As the PL measuring instrument for example, model 25C of Nippon Bunko may be used. When it is combined with, for example, with an Ar laser 4 for a beam light source for foreign matter detection and microscope 11 as a detector of the beam light which is the same as in the foregoing examples, the PL measuring instrument equipped with a positioning function for according to the invention is constituted.

According to the example, the fluorescent spectrum characteristic of inorganic matter and crystallinity is obtained among several foreign matters 7 in the 3 μm level, and the foreign matter is found to be inorganic matter, and the cause of occurrence of the which is related to film forming step and heat treatment step. This analysis is effective in the process for manufacturing semiconductor devices or liquid crystal display devices, in particular in the step relating with film forming, etching, and cleaning.

In this example, the position of the foreign matter is identified by observing the irregular reflection light by the foreign matter in the dark field by the microscope 11, but the same effect is obtained by detecting dark area of the reflected light by means of the microscope 11 installed in the bright field which is the same as in example 2.

Example 7

In the example, as the analyzing unit 3, instead of the metallograph in example 1, a Fluorescent Spectrometer is used, and the other constitution is the same as in FIG. 1, and the positioning operation method is also the same as in example 1.

As the Fluorescent Spectrometer for example, model F-2000 of Hitachi may be used. When it is combined with, for example, an Ar laser 4 for a beam light source for foreign matter detection and microscope 11 as a detector of the beam light which is the same as in the foregoing examples, the Fluorescent Spectrometer apparatus equipped with positioning function of the invention is constituted.

According to the example, the fluorescent spectrum characteristic of inorganic matter is obtained among several foreign matters 7 in 2 μm level, and the foreign matter is found to be an inorganic matter, and the cause of the occurrence of which is related to the film forming step and etching step. This analysis is effective in the process for manufacturing of semiconductor devices or liquid crystal display devices, in particular in the step relating to film forming, etching, and cleaning.

In this example, the position of foreign matter is identified by observing the irregular reflection light by the foreign matter in the dark field by means of the microscope 11, but the same effect is obtained by detecting dark area of the reflected light by means of the microscope 11 installed in the bright field which is the same as in example 2.

Example 8

Figure 6:
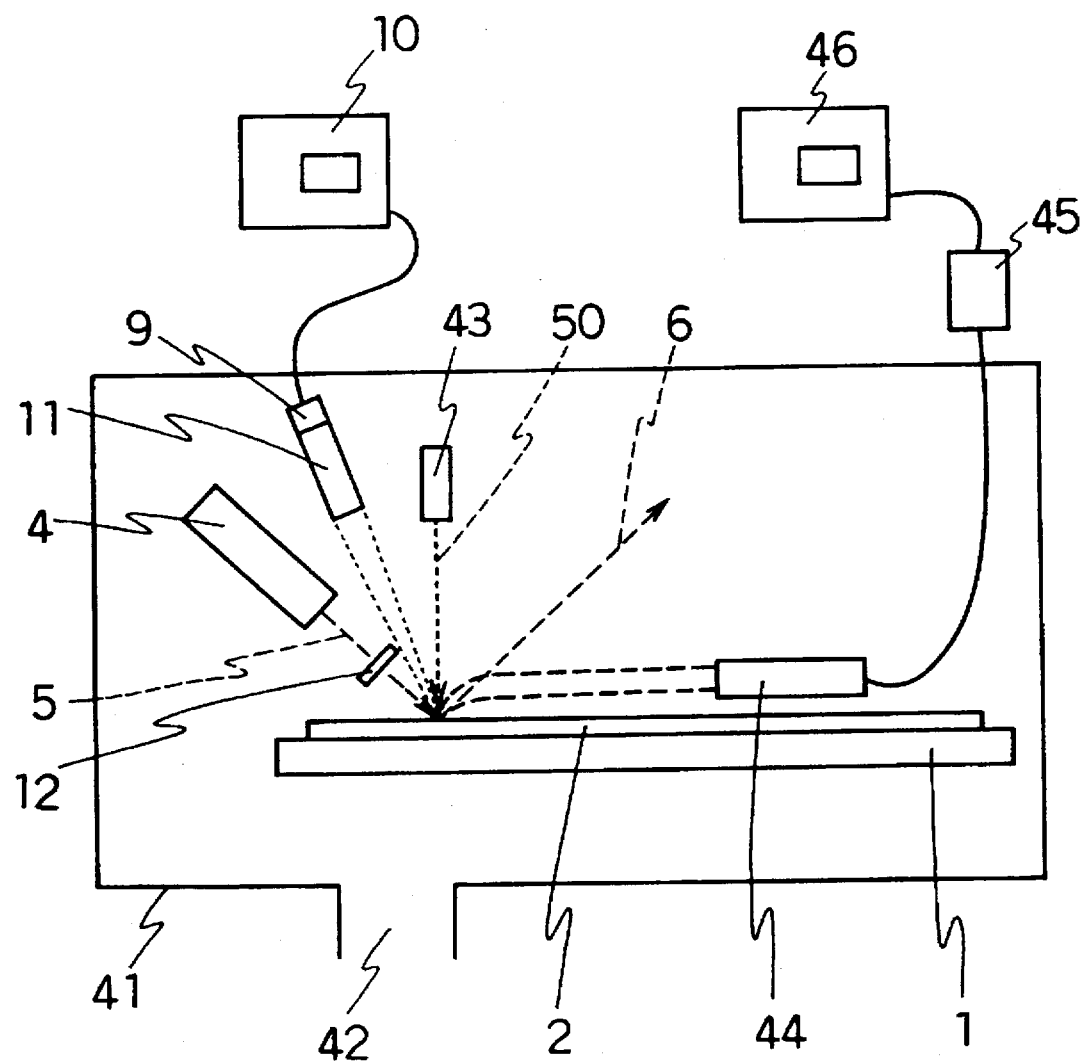
FIG. 6 is an explanatory diagram showing another example of an observation method of the fine foreign matter in accordance with the present invention.

FIG. 6 is an explanatory diagram showing a fundamental constitution of the apparatus used in another example of an analyzing method of the fine foreign matter according to the invention. The difference from example 1 is that the analyzing unit 3 used in FIG. 1 is replaced by a length measuring SEM, for example, model S-7000 of Hitachi. In this example, the analyzing unit 3 comprises, as shown in FIG. 6, an electron gun unit 43 comprising an electron gun and an electron lens for emitting a scanning electron beam 50 to the silicon wafer 2, and a secondary electron detector 44 for transforming the secondary electron generated in the silicon wafer 2 into an electric signal, and the signal obtained in the secondary electron detector 44 is sent into an amplifying and control unit 45 in order to amplify and control the electric signal, and is displayed in a CRT 46 which displays a secondary electron image. Reference numeral 41 is a chamber for keeping them in vacuum, which evacuates through an exhaust port 42 to maintain the vacuum. It is arranged so that both the center of the field of view of the microscope 11 and the center of the scanning range of the scanning electron beam 50 may coincide nearly with each other. Using this length measuring SEM equipped with positioning function, the foreign matter 7 existing on the surface of the silicon wafer 2 can be inspected exactly in the same procedure as in example 1. That is, the SEM apparatus of the invention is equal to a conventional length measuring SEM combined with, for example, an Ar laser 4 for a beam light source for foreign matter detection and microscope 11 as a detector of the beam light.

By observing the irregular reflection light 8 by means of microscope 11, which is the same as in example 1, the existing position of each foreign matter is registered in the coordinates $(x_n, y_m)$ of the x-y actuator 1, and on the basis thereof, moreover, the secondary electron image of each foreign matter 7 is observed by means of the length measuring SEM.

At the same time the foreign matter not discovered by means of the particle counter is detected, and it contributed to elucidation of the cause of the occurrence of foreign matter.

According to the example, sharp SEM images of all foreign matters 7 can be obtained, and various shapes of foreign matters 7, whether bulged or recessed, can be depicted. The analysis of the example is effective in the process for manufacturing of semiconductor devices or liquid crystal display devices, especially in each of the cleaning step, the film forming step, the exposure step, the etching step, the ion implantation step, the diffusion step, and the heat treatment step.

In this example, the position of the foreign matter is identified by observing the irregular reflection light by the foreign matter in the dark field by means of the microscope 11, but the same effect is obtained by detecting dark area of the reflected light by means of the microscope 11 installed in the bright field which is the same as in example 2.

Example 9

Figure 7:
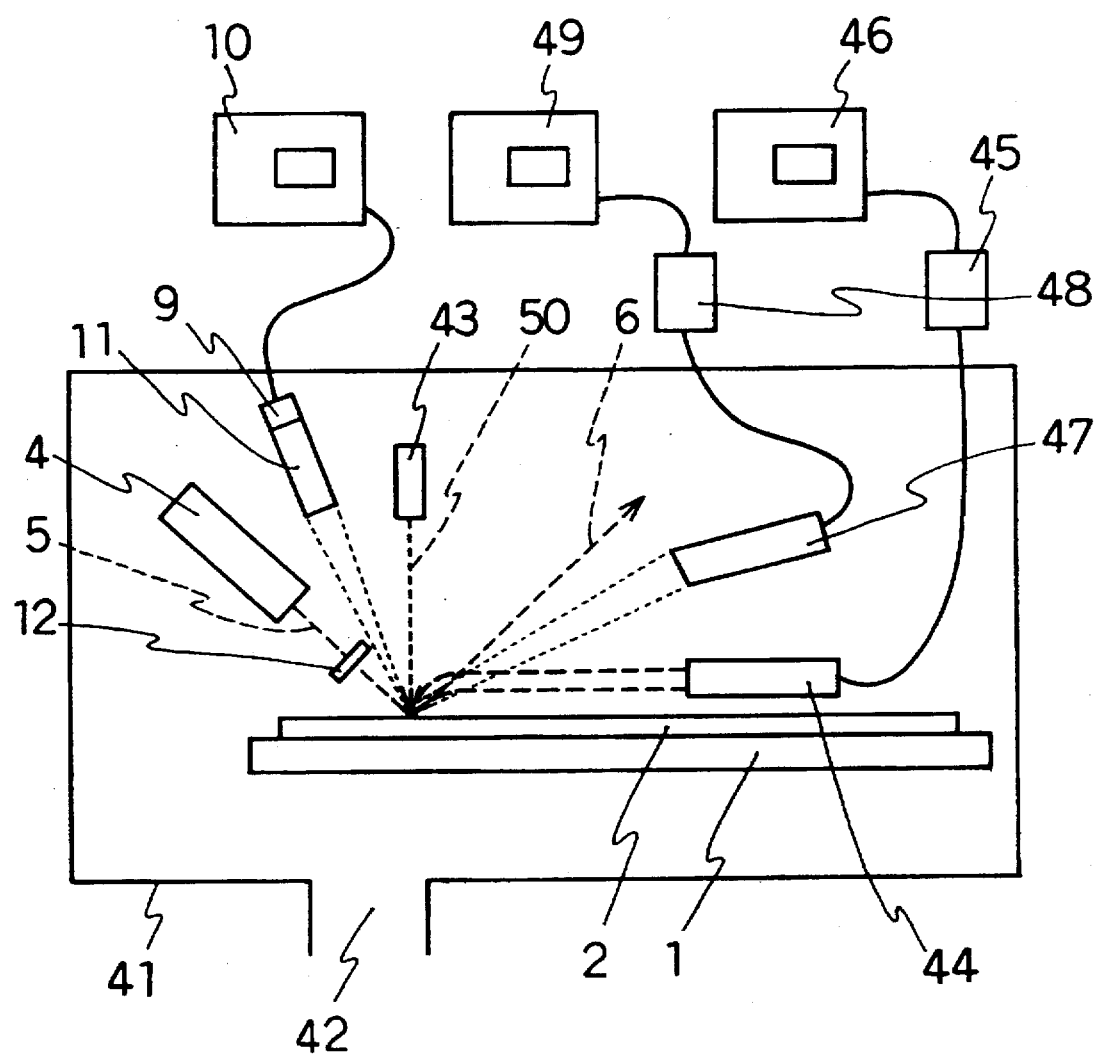
FIG. 7 is an explanatory diagram showing another example of an observation method of the fine foreign matter in accordance with the present invention.

FIG. 7 is an explanatory diagram showing a fundamental constitution of a different example of analyzing method of fine foreign matters of the invention. This example differs from example 8 using SEM in that the constitution in example 8 is newly combined with X-ray detector 47, amplifying and control unit 48 for amplifying and controlling the electric signal obtained from the X-ray detector, and CRT 49 for displaying the X-ray image output. Accordingly, an EPMA equipped with positioning function is formed, but the other parts and configuration are the same as in example 8, and the EPMA apparatus equipped with positioning function of the invention is constituted by combining with, for example, an Ar laser 4 as a beam light source for foreign matter detection and microscope 11 as a detector of the beam light. Both the center of the field of view of the microscope 11 and the center of the scanning range of the scanning electron beam 50 are designed to coincide nearly with each other. In this example, exactly in the same procedure as in example 1, foreign matters 7 existing on the surface of the silicon wafer 2 are inspected, and hence elements are analyzed in the bulged foreign matters 7. As a result in the foreign matters 7, elements of W, Cu, Fe, C, S, O and Cl can be identified, and the cause of the occurrence of the foreign matter is elucidated. However, as for foreign matters 7 of less than 0.3 μm, it takes considerable long detection time for analyzing the elements specifically.

In this example, the position of the foreign matter is identified by observing the irregular reflection light by the foreign matter in the dark field by means of the microscope 11, but the same effect is obtained by detecting dark area of the reflected light by the microscope 11 installed in the bright field which is the same as in example 2.

Example 10

In the example, as the analyzing unit 3, instead of an EPMA in example 9, an AES apparatus is used, and the other constitution is the same as in FIG. 7, and the positioning operation method is also the same as in example 1.

As the AES apparatus, for example, model PHI-670 of Perkin Elmer may be used. When it is combined with, for example, an Ar laser 4 as a beam light source for foreign matter detection and microscope 11 as a detector of the beam light which is the same as in the foregoing examples, the AES electron detector apparatus equipped with positioning function of the invention is constituted.

According to the example, the elements can be analyzed in all bulged foreign matters 7, and the composition of foreign matters 7 can be identified as elements of W, Cu, Fe, C, O, Cl and S, and hence the dust source is identified and the countermeasure is determined. The analysis in the example is effective in the process for manufacturing semiconductor devices or liquid crystal display devices, especially in the steps relating to film forming, etching, exposure, and cleaning.

In this example, the position of the foreign matter is identified by observing the irregular reflection light by the foreign matters in the dark field by means of the microscope 11, but the same effect is obtained by detecting dark area of the reflected light by means of the microscope 11 installed in the bright field which is the same as in example 2.

Example 11

In the example, as the analyzing unit 3, instead of an EPMA in example 9, an EELS is used, and the other constitution is the same as in FIG. 7, and the positioning operation method is also the same as in example 1.

As the EELS for example, model PHI-660 of Perkin Elmer may be used. When it is combined with, for example, an Ar laser 4 as a beam light source for foreign matter detection and microscope 11 as a detector of the beam light which is the same as in the foregoing examples, the EELS apparatus equipped with positioning function of the invention is constituted.

According to the example, compounds can be analyzed in all bulged foreign matters 7, and the chemical bending state of the foreign matters 7 is clarified, and the dust source can be identified, and countermeasures against defects of the apparatus can be determined. The analysis in the example is effective in the process for manufacturing semiconductor devices or liquid crystal display devices, especially in the steps relating to film forming, etching, and exposure.

In this example, the position of the foreign matter is identified by observing the irregular reflection light by the foreign matter in the dark field by means of the microscope 11, but the same effect is obtained by detecting dark area of the reflected light by means of the microscope 11 installed in the bright field which is the same as in example 2.

Example 12

Figure 8:
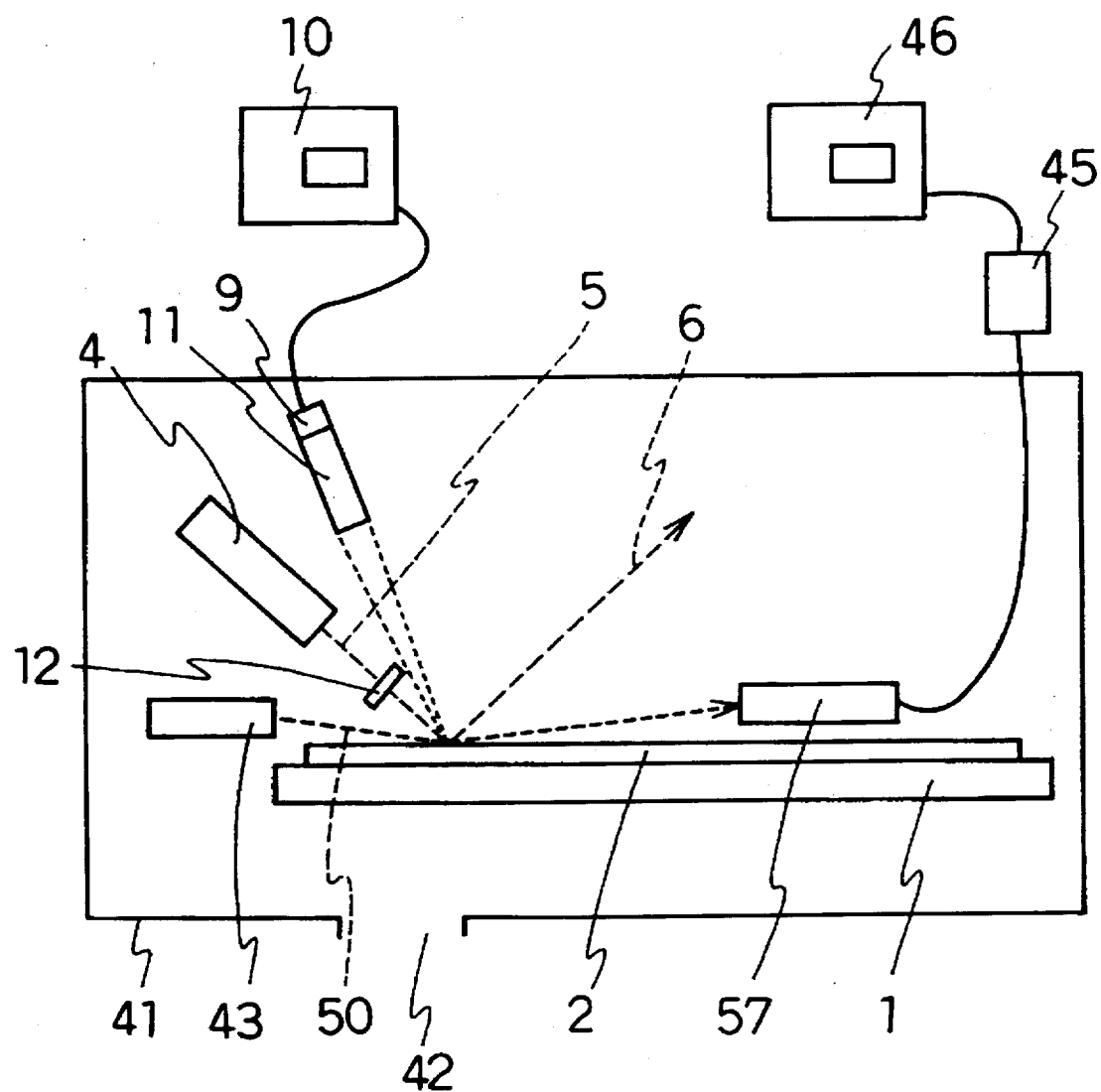
FIG. 8 is an explanatory diagram showing another example of an observation method of the fine foreign matter in accordance with the present invention.
Figure 9:
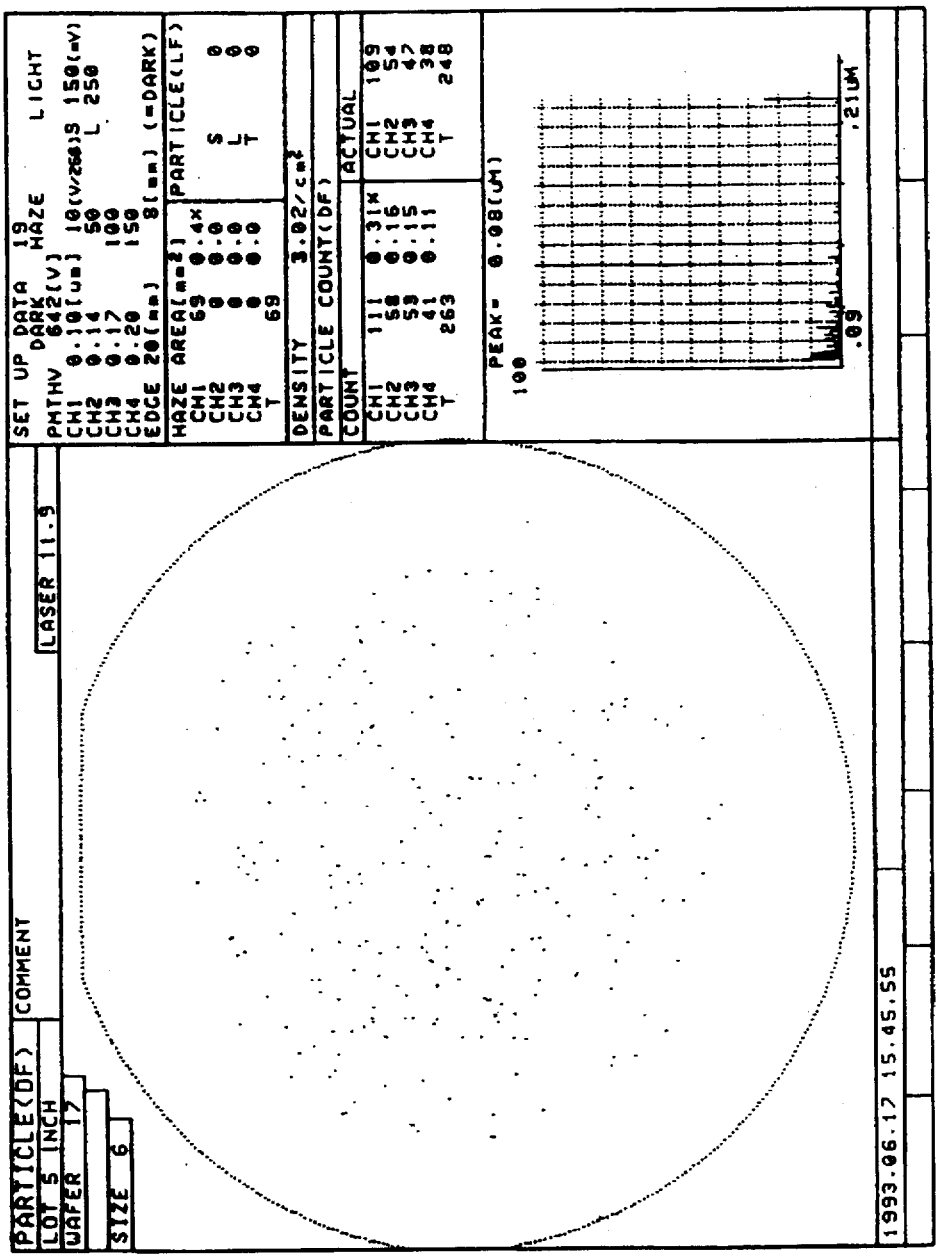
FIG. 9 is a diagram showing the result of measurement of fine foreign matter existing on a silicon wafer by using the particle counter.
Figure 10:
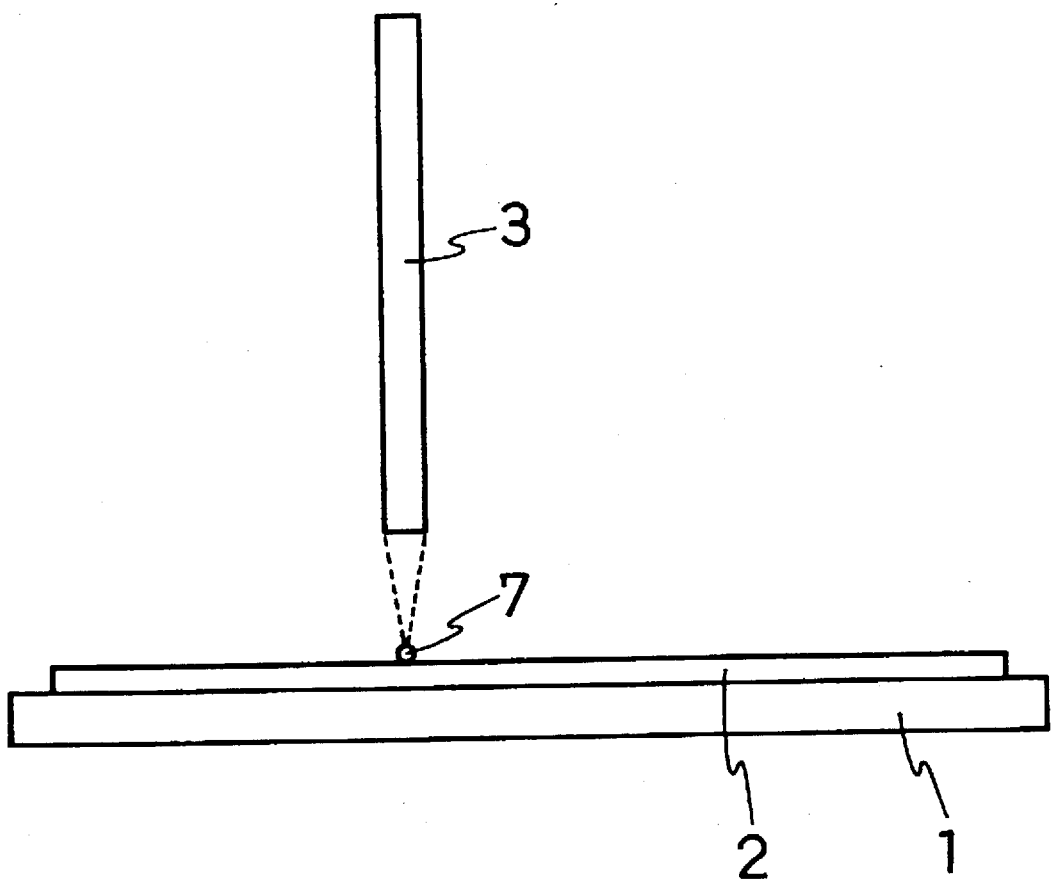
FIG. 10 is an explanatory diagram showing a fundamental structure of a conventional metallograph.

FIG. 8 is an explanatory diagram showing a fundamental constitution of RHEED used in a further different example of analyzing method of fine foreign matter of the invention. The difference in this example from example 8 is as follows. The electron gun unit 48 used in example 8 is inclined to an angle nearly the same as inclination of the secondary electron detector 44 relative to the silicon wafer 2 surface, so that the electron beam 50 barely hits the surface of the silicon wafer 2, and the secondary electron detector 44 is replaced by a CCD camera 57 for obtaining a diffraction spot by electron beam diffracted on the surface of the silicon wafer 2. By means of the RHEED equipped with an actuator of the example, as a result of analysis of foreign matters 7 existing on the surface of the same silicon wafer 2 in the same procedure as in example 1, diffraction spots are obtained in some of the foreign matters 7, and they are found to be crystalline substances, and they can be suppressed in the case of crystalline substances such as whiskers. The analysis in the example is especially effective after the film forming and heat treatment steps in the process for manufacturing of semiconductor devices or liquid crystal display devices, for inhibitory effect of abnormal growth of crystals and selection of conditions thereof.

In this example, the position of the foreign matter is identified by observing the irregular reflection light by the foreign matter in the dark field by means of the microscope 11, but the same effect is obtained by detecting dark area of the reflected light by means of the microscope 11 installed in the bright field which is the same as in example 2.

Example 13

In the example, as the analyzing unit 3, instead of the SEM in example 8, an SIMS is used, that is, the electron gun unit 43 in example 8 has been replaced by an ion gun unit comprising an ion gun and a condenser lens. The surface of the silicon wafer 2 is irradiated with a scanning ion beam, instead of electron ray 50. Moreover the secondary electron detector 44 has been replaced by a mass analysis unit using double convergent mass analyzer or a tetrode mass analyzer in order to isolate and detect secondary ions generated on the surface of the silicon wafer 2. The other constitution is exactly the same as shown in FIG. 6, and the positioning operation method is also the same as in example 1.

As the SIMS, for example, IMS-5F of CAMECA may be used. When it is combined with, for example, an Ar laser 4 as a beam light source for foreign matter detection and microscope 11 as a detector of the beam light, as is the case with the foregoing examples, thus the SIMS apparatus equipped with positioning function of the invention is constituted.

According to the example, the composition of bulged foreign matters 7 can be analyzed, and the cause of the occurrence of foreign matters is elucidated. Consequently, the effect of electric characteristic deterioration due to diffusion of metal from foreign matters is found to lower the yield. The analysis in the example is effective in the process for manufacturing of semiconductor devices or liquid crystal display devices, especially in the steps relating to film forming, heat treatment, etching, and cleaning.

In this example, the foreign matter position is identified by observing the light scattered by the foreign matter in the dark field by the microscope 11, but the same effect is obtained by detecting dark area of the irregularly reflected light by installing the microscope 11 in the bright field, as is the case with in example 2.

Example 14

In the example, instead of the SIMS of example 13, a TOF-SIMS is used, and as a mass analysis unit a mass analyzer of flight time type is used, and the other constitutional and operational manner of detecting dark area of irregularly reflected light from bright field are exactly the same as in example 13.

According to the example, chemical structure analysis of foreign matter is performed by analyzing fragments from foreign matter and moreover, unlike example 13, high molecular matter existing on the outermost surface of foreign matter can be analyzed. Therefore, it is particularly effective for analyzing foreign matter containing organic matter.

Example 15

In this example, PIXE is used instead of SIMS of example 13, and the constitution in example 13 is further combined with an X-ray detector, an amplifying and control unit for amplifying and controlling electric signals which are brought in from the X-ray detector, and a CRT for displaying X-ray image, thereby composing the PIXE apparatus. The other constitution and operational manner of detecting dark area of irregular reflection light from bright field are exactly the same as in example 13.

According to the example, the composition of foreign matter can be analyzed, and it is particularly suited to elementary analysis at high sensitivity and with great precision. Therefore, it is particularly effective for analysis of foreign matter of very small particle size of less than 0.1 µm.

Example 16

In the example, instead of the electron gun unit 43 in example 8, an ion gun unit comprising an ion gun and a condenser lens is used, and an FIB is composed for removing undesired foreign matters by irradiating scanning ion beams. The other constitutional and the operational manner of detecting dark area of irregular reflection light from bright field are exactly the same as in example 8.

According to the example, while observing fine foreign matter, undesired foreign matter can be removed, and it is effective to repair them immediately, it is therefore particularly effective for analyzing foreign matters in order to enhance the yield by eliminating defects due to foreign matters.

Example 17

In the example, the electron gun unit 43 in example 11 is replaced by an XPS equipped with positioning function using soft X-ray such as AlKα, MgKα or the like and the other constitutional and the operational manner of detecting dark area of irregular reflection light from bright field are exactly the same as in example 11.

According to the example, the chemical bond analysis of bulged foreign matters can be performed. Since X-ray beam is used in this example, in particular, damage to the specimens is less. Therefore, without destroying, it is effective for analyzing the outermost surface of the foreign matters in the order of tens of angstroms of depth, in particular.

Example 18

The example relates to a UPS equipped with positioning function using an ultraviolet beam unit generated from a high pressure mercury lamp and shaped in a beam form, instead of the electron gun unit 43 in example 11, and the other constitutional and the operational manner of detecting dark area of irregular reflection light from bright field are exactly the same as in example 11.

In this example, too, the composition of bulged foreign matters can be analyzed. Since the ultraviolet beam is used in this example, in particular, it is effective that damage to the specimens is less. As damage to the specimens is suppressed, it is effective for analyzing the outermost surface of the foreign matters in the order of several angstroms, in particular.

In all foregoing examples a silicon wafer 2 is used as specimens, but the same effects are obtained by using other flat substrates such as insulating transparent substrates (even if there are certain roughness on the surface), and the specimens are not limited to silicon wafers alone.

Example 19

The example relates to an example of manufacturing method of semiconductor devices, in which the foreign matter on the surface of the semiconductor wafers are analyzed by means of the AES apparatus, among the analyzing apparatuses of the invention mentioned above, in the manufacturing process for the semiconductor device.

For example, the position of the foreign matter on a silicon wafer which is cleaned in the cleaning apparatus in manufacture line is observed roughly by the conventional particle counter.

Next, on the x-y stage of the AES apparatus, the silicon wafer is placed. The definition of x-y coordinates is defined as follows. The flat line direction of the orientation flat of the wafer is to be the x-axis and three points on the wafer outermost circumference (avoiding the orientation flat portion) are measured and the wafer center position is defined as (0, 0).

The correlation of the x, y coordinates on the x-y stage of the particle counter and the AES apparatus is limited to around ±100 to ±500 µm. In the region near the x,y coordinates of the existing position of the fine foreign matters investigated by means of the particle counter, the foreign matter detection beam light of the AES apparatus is irradiated, and the position of the fine foreign matter is accurately specified in the above method. Between the x, y coordinates of the particle counter and AES apparatus, as mentioned above, a deviational error of about ±100 to ±500 µm occurs, but the foreign matter detection beam light has a spot diameter of about a range 2,000 to 5,000 µm, which is capable of covering the deviation in position, so that the position of fine foreign matter can be easily determined accurately.

In the inspection by the conventional particle counter, only the presence of a relatively large foreign matter can be known, and it is far from possible to judge if the foreign matter will adversely affect the semiconductor elements or not. According to the invention, however, while the position of the fine foreign matter can be accurately detected, the element of the foreign matter can be identified by means of the AES apparatus. For example, if the foreign matter element is Si or O, it does not cause trouble in the process, but if it is Fe, Cu, Na, Mo, or K, it may cause deterioration of electric characteristics, which is not desired from the viewpoint of reliability.

In order to improve the deterioration, products which have been passed through a process having dust sources of Fe, Cu, Na, Mo, K or the like are cleaned separately in other cleaning apparatus from products which have been passed through a process other than those above.

The deterioration of electric characteristics which is caused by such elements can be suppressed thereby ensuring to stabilize the process.

In the example, the inspection step after cleaning is explained, but in manufacture of semiconductor devices, various steps are repeated, such as ion diffusion, film formation, exposure and etching, or the like and in each step the fine foreign matter can be similarly inspected by sampling or by 100%.

In the example, the AES apparatus is used as the analyzer, but it is also possible to analyze by other apparatuses mentioned above than the AES apparatus.

According to the example, in the manufacturing process of semiconductor devices, fine foreign matters on the semiconductor wafer can be accurately identified, and the results can be fed back to the manufacturing process to improve the yield, and defective pieces can be rejected, thereby enhancing the yield and improving the reliability in manufacture of super-LSI.

Moreover according to the example, even tiny foreign particles of less than 0.1 μm that can not be detected by the conventional particle counter can be identified, and a smaller foreign matter near the fine foreign matter discovered by the particle counter can be inspected, and it may help to elucidate the cause of the occurrence of fine foreign matter discovered by the particle counter.

Example 20

The example relates to an example of method of manufacturing liquid crystal display devices, in which the foreign matter on the surface of insulating transparent substrates are analyzed by means of the AES apparatus, among the analyzing apparatuses of the invention mentioned above.

That is, the liquid crystal display devices are manufactured by adhering a thin film transistor (TFT) substrate comprising TFT as switching element of each pixel and gate wiring, source wiring and pixel electrode provided among pixels, and a counter substrate comprising counter electrodes and others, on an insulating transparent substrate of glass or the like on the circumference while keeping a specific clearance, and injecting liquid crystal material in the clearance. In the recent liquid crystal display devices, to meet the requests for higher definition and increase of aperture rate, the gate wiring and signal wiring tend to be narrower, the clearance to the pixel electrode is narrower, and breakage of signal wiring and shorting of wiring are likely to occur.

In the invention, in the manufacturing process of this TFT substrate, various steps such as film forming, exposure and etching are involved, and, for example, in order to form the gate electrode and gate wiring, a metal film of tungsten or the like was formed on the entire surface of the insulating transparent substrate in a thickness of abut 0.1 to 1 μm, and the foreign matter on the film forming surface is inspected and analyzed by means of the AES apparatus.

As is the case with semiconductor wafers, rough positioning of foreign matters existing on the film forming surface are investigated by the particle counter. Then, the insulating transparent substrate is positioned and mounted on the x-y stage of the AES apparatus equipped with positioning function as the analyzer by reference to the positioning mark.

The correlation of the x, y coordinates on the x-y stage between the particle counter and the AES apparatus equipped with positioning function is limited within around ±100 to ±500 μm, and as is the case with example 19, the positions of fine foreign matters can be identified accurately.

Afterwards, as a result of analysis of foreign matter by means of AES apparatus equipped with positioning function, the composition is known. According to the result, foreign matter containing elements other than tungsten has been found. By investigation for elements other than tungsten presence of a dust source due to parts used in a film forming apparatus is revealed. By exchanging the parts, the occurrence of foreign matter can be suppressed. Therefore, by feeding back the result to the manufacturing process so that such foreign matter except tungsten may not be produced, defects due to foreign matter can be decreased.

In the example, the analysis of forming tungsten film for forming wiring is explained, but after any step such as insulating film forming step and etching step, it is possible to analyze by sampling or by 100% testing.

In the example, the AES apparatus is used as the analyzer, but it is also possible to analyze by other apparatuses than the AES apparatus.

According to the example, in the process for manufacturing liquid crystal display devices, fine foreign matter on the insulating transparent substrate can be accurately identified, and it may be improved by feeding information back to the manufacturing process, and moreover defective pieces can be eliminated, and a high yield is obtained and the reliability is enhanced in the liquid crystal display devices of superfine definition and multiple pixels.

As described herein, according to the invention, for the fine foreign matter positioned on the coordinates of the particle counter, the position of the fine foreign matter can be registered precisely in the coordinates of other analyzer, and depending on the positioning method of fine foreign matter, if there is a coordinate deviation of thousands microns due to linking between the conventional particle counter and the analyzer, by observing the beam light change by spot irradiation in the range on the sample surface covering it, the existing position of the fine foreign matter can be detected again, and the position of the fine foreign matter can be identified accordingly, thereby making it possible to position accurately and immediately in the precise coordinates.

Even if the intended fine foreign matter cannot be detected by the particle counter, according to the analyzer of the invention the position of the fine foreign matter can be newly detected and can be determined, thereby making it possible to position accurately and immediately in the precise coordinates.

According to the analyzing method of fine foreign matter of the invention, by emitting the beam light for detection of fine foreign matters in spot irradiation, and observing the change in the beam light due to the fine foreign matter, the fine foreign matter is detected, and its position is determined, so that the particle ray can be accurately hit against the fine foreign matter, and the shape, chemical structure, crystal structure and elementary composition of the fine foreign matter can be analyzed, and the cause of the occurrence of foreign matter can be easily elucidated and its countermeasure can be easily determined, and if necessary, bulged foreign matter can be removed, thereby enhancing the production yield and reliability.

By employing the analyzer of the invention, each analyzing method can be effected easily, and surface observation and composition analysis can be done selectively only in the existing range of fine foreign matter, and therefore the measuring time can be shortened notably, and the quality of the material may be evaluated in a short time.

Therefore, by applying into the manufacturing process of semiconductor devices and manufacturing process of liquid crystal devices, the effects of foreign matter on the fine pattern can be prevented, so that the semiconductor devices and liquid crystal display devices enhanced in the yield and reliability can be obtained.

What is claimed is:

1. A method of detecting the position of a fine foreign matter on a surface of a sample comprising the steps of:
   (a) determining a position of the fine foreign matter on the surface of the sample using a particle counter,
   (b) transferring the sample onto a coordinate stage of an analyzer,
   (c) roughly linking the position determined by the particle counter with a coordinate of a coordinate system on the coordinate stage of the analyzer, (d) irradiating a spot of beam light to a partial region on the surface of the sample, the partial region defined by the spot of beam light encompassing the coordinate relating to the position of the fine foreign matter determined by the particle counter, (e) detecting again the position of the fine foreign matter by observing a change in the beam light caused by the fine foreign matter, and (f) registering the position of the fine foreign matter detected again in the coordinates of the analyzer.

2. A method of analyzing content of a fine foreign matter on a surface of a sample comprising the steps of:

(a) determining a position of the fine foreign matter on the surface of the sample using a particle counter, (b) transferring the sample onto a coordinate stage of an analyzer, (c) roughly linking the position determined by the particle counter with a coordinate of a coordinate system on the coordinate stage of the analyzer, (d) irradiating a spot of beam light to a partial region on the surface of the sample, the partial region defined by the spot of beam light encompassing the coordinate relating to the position of the fine foreign matter determined by the particle counter, (e) detecting again the position of the fine foreign matter by observing a change in the beam light caused by the fine foreign matter, (f) registering the position of the fine foreign matter detected again in the coordinate of the analyzer, (g) moving a portion of the surface of the sample which includes the position of the fine foreign matter detected again to the spot irradiated by the beam light at the position of the fine foreign matter, and (h) analyzing the content of the fine foreign matter.

3. The method of claim 2, wherein a diameter of the spot of the beam light includes a whole area of a region of probable deviational aberration when an information of a measured position obtained in the particle counter is transmitted to the analyzer.

4. The method of claim 2, wherein the beam light is a laser light.

5. The method of claim 2, wherein the beam light is an S-polarized light.

6. The method of claim 2, wherein detecting the position of the fine foreign matter detected again is carried out by means of detecting irregularly reflected light.

7. The method of claim 2, wherein detecting the position of the fine foreign matter detected again is carried out by means of detecting a dark area caused by the irregularly reflected light within a bright field of the beam light.

8. The method of claim 2, wherein detecting the position of the fine foreign matter detected again is carried out by observing by means of a microscope and a focus of the microscope is matched to the spot of the beam light.

9. The method of claim 8, wherein a CCD camera is attached to an eyepiece of the microscope.

10. The method of claim 9, wherein an image intensifier is mounted on the CCD camera.

11. The method of claim 8, wherein a region of a field of view is wider than an area of a region of deviational aberration.

12. The method of claim 2, wherein detecting the position of the free foreign matter detected again is carried out by using a photodetector.

13. The method of claim 12, wherein a region of the sample surface in which the photodetector detects reflected light is wider than the area of a region of deviational aberration.

14. The method of claim 2, wherein the sample is a semiconductor device in processing or a semiconductor wafer on which the semiconductor device is being formed.

15. The method of claim 2, wherein the sample is an insulating transparent substrate in processing on which a liquid crystal display device is being formed.

16. The method of claim 2, wherein the analyzer is a metallograph.

17. The method of claim 2, wherein the analyzer comprises a Scanning Laser Microscope.

18. The method of claim 2, wherein the analyzer comprises a Microscope Infrared Spectrometer wherein chemical structure is analyzed.

19. The method of claim 2, wherein the analyzer comprises a Microscope Raman Spectrometer wherein chemical structure is analyzed.

20. The method of claim 2, wherein the analyzer comprises a Photoluminescence Spectrometer wherein spectroscopic analysis is carried out.

21. The method of claim 2, wherein the analyzer comprises a spectrometer wherein microanalysis of trace elements is carried out.

22. The method of claim 2, wherein the analyzer comprises a Scanning Electron Microscope.

23. The method of claim 2, wherein the analyzer comprises an Electron Probe Micro-Analyzer wherein microanalysis of trace elements on surface is carried out.

24. The method of claim 2, wherein the analyzer comprises a Scanning Auger Electron Spectrometer wherein microanalysis of trace elements on surface is carried out.

25. The method of claim 2, wherein the analyzer comprises an Electron Energy-Loss Spectrometer wherein surface analysis of trace elements is carried out.

26. The method of claim 2, wherein the analyzer comprises a Reflection High Energy Electron Diffraction wherein crystal structure analysis is carried out.

27. The method of claim 2, wherein the analyzer comprises a Secondary Ion Mass Spectrometer wherein microanalysis of trace elements on surface is carried out.

28. The method of claim 2, wherein the analyzer comprises a Time Of Flight-SIMS wherein microanalysis of trace elements on surface is carried out.

29. The method of claim 2, wherein the analyzer comprises a Particle Induced X-ray Emission wherein microanalysis of trace elements on surface is carried out.

30. The method of claim 2, wherein the analyzer comprises a Focused Ion Beam instruments wherein surface processing is performed.

31. The method of claim 2, wherein the analyzer comprises an X-ray Photoelectron Spectrometer wherein chemical structure analysis is carried out.

32. The method of claim 2, wherein the analyzer comprises an Ultraviolet Photoelectron Spectroscope wherein chemical analysis is carried out.

33. A system for determining the position of fine foreign matter on a surface of a sample comprising:

a device for determining a position of the fine foreign matter on the surface of the sample, means for roughly linking the position determined by the device for determining with a coordinate of a coordinate system on a coordinate stage of an analyzer, a beam light source for irradiating a spot of beam light to a partial region on the surface of the sample, the partial region defined by the spot of beam light encompassing the coordinate relating to the position of the fine foreign matter determined by the device for determining, a detector for detecting again the position of the fine foreign matter by observing a change in the beam light caused by the fine foreign matter, and means for registering the position of the fine foreign matter detected again in the coordinates of the analyzer.

34. The system of claim 33, wherein the source of the beam is a laser light source.

35. The system of claim 33, wherein the detector of beam light is a microscope.

36. The system of claim 33, wherein the detector of beam light is a photodetector.

37. The system of claim 33, wherein the analyzer comprises a metallograph.

38. The system of claim 33, wherein the analyzer comprises a Scanning Laser Microscope.

39. The system of claim 33, wherein the analyzer comprises a Microscope Fourier Transform Infrared Spectrometer.

40. The system of claim 33, wherein the analyzer comprises a Microscope Raman Spectrometer.

41. The system of claim 33, wherein the analyzer comprises a Photoluminescence Spectrometer.

42. The system of claim 33, wherein the analyzer comprises a spectrometer.

43. The system of claim 33, wherein the analyzer comprises a Scanning Electron Microscope.

44. The system of claim 33, wherein the analyzer comprises an Electron Probe Micro-Analyzer.

45. The system of claim 33, wherein the analyzer comprises an Auger Electron Spectrometer.

46. The system of claim 33, wherein the analyzer comprises an Electron Energy-Loss Spectrometer.

47. The system of claim 33, wherein the analyzer comprises a Reflection High Energy Electron Diffraction.

48. The system of claim 33, wherein the analyzer comprises a Secondary Ion Mass Spectrometer.

49. The system of claim 33, wherein the analyzer comprises a Time Of Flight-SIMS.

50. The system of claim 33, wherein the analyzer comprises a Particle Induced X-ray Emission.

51. The system of claim 33, wherein the analyzer comprises a Focused Ion Beam instruments.

52. The system of claim 33, wherein the analyzer comprises an X-ray Photoelectron Spectrometer.

53. The system of claim 33, wherein the analyzer comprises an Ultraviolet Photoelectron Spectrometer.

54. A method for manufacturing semiconductor devices comprising the steps of at a least cleaning step, a film forming step, an exposure step, an etching step, an ion implantation step, a diffusion step, and a heat treatment step wherein at least one of the steps is accompanied by inspection substeps, at least one of the substeps being an analysis substep wherein an analysis for analyzing content of a foreign matter is carried out by means of a method comprising the steps of:

(a) determining a position of the fine foreign matter on a sample surface using a particle counter, (b) transferring the sample onto a coordinate stage of an analyzer, (c) roughly linking the position determined by the particle counter with a coordinate of a coordinate system on the coordinate stage of an analyzer, (d) irradiating a spot of beam light to a partial region on the sample surface including the coordinate relating to the position of the free foreign matter determined by the particle counter, (e) detecting again the position of the fine foreign matter by observing a change in the beam light caused by the fine foreign matter, (f) registering the position of the fine foreign matter detected again in the coordinate of the analyzer, (g) moving a portion of the surface of the sample which includes the position of the fine foreign matter detected again to the spot irradiated by the beam light at the position of the fine foreign matter, and (h) analyzing the content of the fine foreign matter.

55. A method for manufacturing semiconductor devices comprising the steps of at least a cleaning step, a film forming step, an exposure step, an etching step, an ion implantation step, a diffusion step, and a heat treatment step wherein at least one of the steps is accompanied by inspection substeps, at least one of the substeps being an analysis substep, wherein an analysis for analyzing a foreign matter is carried out by means of an analyzer for analysis of a surface condition of the sample by irradiating a particle beam toward both an x-y stage which can be moved at least longitudinally and laterally and the sample located on the x-y stage, and observing a secondary particle beam emitted from the sample in response to being irradiated by the particle beam at at least one position, further comprising the steps of:

(a) irradiating a spot of beam light from a beam light source for foreign matter detection on the sample surface in the vicinity of said at least one position, and (b) detecting with a detector a change in the spot of beam light from the source of the spot of beam light caused by the foreign matter on the sample surface.

56. A method for manufacturing liquid crystal display devices comprising:

(a) adhering a TFT substrate of a first insulating transparent substrate on which at least thin film transistors and pixel electrodes are provided, and a counter substrate of a second insulating transparent substrate on which counter electrodes are provided, on their circumference while keeping a specific clearance between the two substrates, and (b) injecting liquid crystal material in the clearance, the method further includes a cleaning step, a film forming step, an exposure step, an etching step, an ion implantation step, and a heat treatment step, for manufacturing the TFT substrate and the counter substrate, at least one of the steps is accompanied by inspection substeps, at least one of the substeps is an analysis substep wherein an analysis for analyzing content of the foreign matter is carried out by means of method comprising the steps of:

(1) determining a position of a fine foreign matter on a sample surface using a particle counter, (2) transferring the sample onto a coordinate stage of an analyzer, (3) roughly linking the position determined by the particle counter equipped with a coordinate of a coordinate system on the coordinate stage of the analyzer, (4) irradiating a spot of beam light to a partial region on the sample surface including the coordinate relating to the position of the fine foreign matter determined by the particle counter, (5) detecting again the position of the fine foreign matter by observing a change in the beam light caused by the fine foreign matter, (6) registering the position of the fine foreign matter detected again in the coordinates of the analyzer, (7) moving a portion of the surface of the sample which includes the position of the fine foreign matter detected again to the spot irradiated by the beam light at the position of the free foreign matter, and (8) analyzing the content of the fine foreign matter.

57. A method for manufacturing liquid crystal display devices comprising:

(a) adhering a TFT substrate of a first insulating transparent substrate on which at least thin film transistors and pixel electrodes are provided, and a counter substrate of a second insulating transparent substrate on which counter electrodes are provided, on their circumference while keeping a specific clearance between the two substrates, and (b) injecting liquid crystal material in the clearance, wherein the method further includes a cleaning step, a film forming step, an exposure step, an etching step, an ion implantation step, and a heat treatment step, for manufacturing the TFT substrate and the counter substrate, at least one of the steps being accompanied by inspection substeps, and at least one of said substeps is an analysis substep, wherein an analysis for analyzing the foreign matter is carried out by means of an analyzer for analysis of a surface condition of the sample by irradiating a particle beam toward both an x-y stage which can be moved at least longitudinally and laterally and the sample located on the x-y stage, and observing a secondary particle beam emitted from the sample in response to being irradiated by the particle beam at at least one position, further comprising the steps of:

(1) irradiating a spot of beam light from a beam light source for foreign matter detection on the sample surface in the vicinity of said at least one position, and (2) detecting with a detector a change in the spot of beam light from the source of the spot of beam light caused by the foreign matter on the sample surface.

58. An analyzer for analyzing a surface of a sample for the presence of fine foreign matter on the basis of separately acquired position information, comprising:

a beam light source for irradiating a spot of beam light to a partial region on the surface of the sample, the partial region defined by the spot of beam light encompassing a coordinate relating to a position of fine foreign matter corresponding to said separately acquired position information, a detector for detecting the position of the fine foreign matter by observing a change in the beam light caused by the fine foreign matter, means for registering the position of the fine foreign matter detected by said detector in the coordinates of the analyzer, a particle beam source for directing a beam of particles to said surface of said sample, and a particle beam detector for detecting said beam of particles after said beam impinges on said surface of said sample.

59. An analyzer for analyzing a surface of a sample for the presence of fine foreign matter on the basis of separately acquired position information, comprising:

a beam light source for irradiating a spot of beam light to a partial region on the surface of the sample, the partial region defined by the spot of beam light encompassing a coordinate relating to a position of fine foreign matter corresponding to said separately acquired position information, a detector for detecting the position of the fine foreign matter by observing a change in the beam light caused by the fine foreign matter, and means for registering the position of the fine foreign matter detected in the coordinates of the analyzer.

* * * * *